United States Patent [19]

Crimmin et al.

[11] Patent Number: 5,525,629

[45] Date of Patent: Jun. 11, 1996

[54] INHIBITION OF CYTOKINE PRODUCTION

[75] Inventors: Michael J. Crimmin; William A. Galloway; Andrew J. Gearing, all of Oxford, United Kingdom

[73] Assignee: British Bio-Technology Limited, Oxford, England

[21] Appl. No.: 146,083

[22] PCT Filed: Apr. 5, 1993

[86] PCT No.: PCT/GB93/00706

§ 371 Date: Nov. 4, 1993

§ 102(e) Date: Nov. 4, 1993

[87] PCT Pub. No.: WO93/20047

PCT Pub. Date: Oct. 14, 1993

[30] Foreign Application Priority Data

Dec. 17, 1992 [GB] United Kingdom .................. 9207759
Jan. 15, 1993 [GB] United Kingdom .................. 9226337
Apr. 5, 1993 [GB] United Kingdom .................. 9300701

[51] Int. Cl.$^6$ ................................................ A61L 31/235
[52] U.S. Cl. ................ 514/542; 514/562; 514/513; 514/556; 558/254; 560/13; 560/17; 560/16; 560/149; 560/152; 562/431; 562/430; 562/556
[58] Field of Search .................................. 514/513, 550, 514/562, 542; 560/13, 17, 16, 152, 140; 562/431, 430, 556; 558/254

[56] References Cited

U.S. PATENT DOCUMENTS 4,599,361  7/1986  Dickens et al. .
5,310,763  5/1994  Campion et al. ................ 514/575

FOREIGN PATENT DOCUMENTS

0236872A3  9/1987  European Pat. Off. .
0274453A3  7/1988  European Pat. Off. .
0489577A1  6/1992  European Pat. Off. .
0489579A1  6/1992  European Pat. Off. .
0497192A2  8/1992  European Pat. Off. .
WO90/05716  5/1990  WIPO .
WO90/05719  5/1990  WIPO .
WO91/02716  3/1991  WIPO .
WO92/13831  8/1992  WIPO .

OTHER PUBLICATIONS

Jue et al. (1990), *Biochemistry*, vol. 29, pp. 8371–8377.
Mathison et al. (1988), *J. Clin. Invest.*, 81, pp. 1925–1937.
Miethke et al. (1992), *J. Exp. Med.*, vol. 175, 91–98.
Grau et al. (1989), *Immunol. Rev.*, 112, pp. 49–70.
Barnes et al. (1992), *Infect. and Imm.*, vol. 60, pp. 1441–1446.
Endres et al. (1991), *Immunol.*, 72, pp. 56–60.
Schandene et al. (1992), *Immunol.*, 76, pp. 30–34.

Alegre et al. (1991), *Transplantation*, vol. 52, pp. 674–679.
Bianco et al. (1991), *Blood*, vol. 78, pp. 1205–1211.
Sampajo et al. (1991), *J. Exp. Med.*, vol. 173, pp. 699–703.
Bagby et al. (1991), *J. Infect. Dis.*, vol. 163, pp. 83–88.
Charpentier et al., (1991), *Presse-med.*, vol. 20, pp. 2009–2011.
Silva et al. (1990), *J. Infect. Dis.*, vol. 162, pp. 421–427.
Franks et al. (1991), *Infect. Immun.*, vol. 59, pp. 2609–2614.
Tracey et al. (1987), *Nature*, vol. 330, pp. 662–664.
Lesslauer et al. (1991), *Eur. J. Immunol*, vol. 21, pp. 2883–2886.
Ashkenazi et al. (1991), *Proc. Nat'l Acad. Sci. USA*, vol. 88, pp. 10535–10539.
Cawston et al. (1979), *Anal. Biochem.*, vol. 99, pp. 340–345.
Cawston et al. (1981), *Methods in Enzymology*, vol. 80, pp. 711–722.
Cawston et al. (1981), *Biochem. J.*, vol. 195, pp. 159–165.

*Primary Examiner*—José G. Dees
*Assistant Examiner*—Samuel Barts
*Attorney, Agent, or Firm*—Banner & Allegretti, Ltd.

[57] ABSTRACT

Hydroxamic acid derivatives of formula (I):

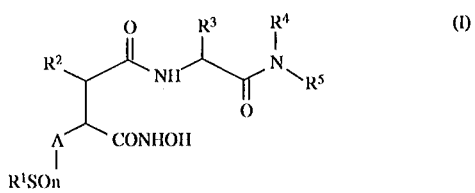

wherein $R^1$ represents hydrogen or an ($C_1$–$C_6$)alkyl, ($C_1$–$C_6$)alkoxycarbonyl($C_1$–$C_6$)alkyl, phenyl, substituted phenyl, phenyl($C_1$–$C_6$)alkyl, heterocyclyl, ($C_1$–$C_6$)alkylcarbonyl, phenacyl or substituted phenacyl group;

$R^2$ represents hydrogen or a ($C_1$–$C_6$)alkyl, ($C_2$–$C_6$)alkenyl, phenyl($C_1$–$C_6$)alkyl, cycloalkyl($C_1$–$C_6$)alkyl or cycloalkenyl($C_1$–$C_6$)alkyl group, $R^3$ represents a group —$CH_2CO_2(C_1$–$C_4)$alkyl or —$CH_2CH_2CO_2$ ($C_1$–$C_4$)alkyl;

$R^4$ represents hydrogen or a ($C_1$–$C_6$)alkyl or phenyl($C_1$–$C_6$)alkyl group;

$R^5$ represents hydrogen or a methyl group;

n is 0, 1 or 2;

and A represents a ($C_1$–$C_6$)hydrocarbon chain optionally substituted with one or more ($C_1$–$C_6$)alkyl, phenyl, or substituted phenyl groups;

or a salts, solvates or hydrates thereof, are inhibitors of tumour necrosis factor production and of matrix metalloproteinases.

23 Claims, No Drawings

INHIBITION OF CYTOKINE PRODUCTION

This application was filed under U.S.C. 371 of the application PCT/GB93/00708 filed Apr. 5, 1993.

This invention relates to therapeutically active hydroxamic acid derivatives, to processes for their preparation, to pharmaceutical compositions containing them, and to the use of such compounds in medicine. In particular, the compounds are inhibitors of the release of tumour necrosis factor (TNF) from cells, and inhibitors of metalloproteinases involved in tissue degradation.

TNF is a cytokine which is produced initially as a cell-associated 28 kD precursor. It is released as an active, 17 kD form (Jue, D-M et al., (1990) Biochemistry 29:8371–8377), which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Preventing the production or action of TNF is, therefore, predicted to be a potent therapeutic strategy for many inflammatory, infectious, immunological or malignant diseases. These include, but are not restricted to, septic shock, haemodynamic shock and sepsis syndrome (Mathison et al. (1988) J. Clin. Invest. 81:1925–1937; Miethke et al. (1992) J. Exp. Med. 175:91–98), post ischaemic reperfusion injury, malaria (Grau et al, (1989) Immunol. Rev. 112:49–70); mycobacterial infection (Barnes et al. (1992) Infect. Imm. 60:1441–6), meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Current clinical anti-TNF strategies involve the use of corticosteroids such as dexamethasone, and the use of cyclosporin-A or FK506, which are non-specific inhibitors of cytokine gene transcription. Phosphodiesterase inhibitors such as pentoxyfilline have been shown to be more specific inhibitors of TNF gene transcription (Endres Set al. (1991) Immunol. 72:56–60, Schandene et al. (1992) Immunol. 76:30–34, Alegre ML, et al. (1991); Transplantation 52:674–679, Blanco et al. (1991) Blood 78:1205–1211). Thalidomide has also been shown to inhibit TNF production by leucocytes (Sampajo et al, (1991) J. Exp. Med. 173:699–703). In experimental settings, anti-TNF monoclonal antibodies, soluble TNF receptors and soluble TNF receptor/immunoadhesins have been shown to specifically inhibit the effects of TNF action (Bagby et al. (1991) J. Infect. Dis. 163:83–88, Charpentier et al. (1991) Pressemed. 20:2009–2011, Silva et al. (1990) J. Infect. Dis. 162:421–427; Franks et al. (1991) Infect. Immun. 59:2609–2614, Tracey et al. (1987) Nature 330:662–664; Fischer et al. (1992) PNAS USA in press, Lesslauer et al. (1991) Eur. J. Immunol. 21:2883–2886, Ashkenazi et al. (1991) PNAS USA 88:10535–10539)

It has recently been shown that the effects of TNF are mediated by two peptides, TNF α and TNF β. Although these peptides have only 30% homology with each other, they activate the same receptors and are encoded by immediately adjacent genes. As used herein, the term tumour necrosis factor or TNF therefore means tumour necrosis factor α and peptides having a high degree of sequence homology with, or substantially similar physiological effects to, TNF α, for example TNF β.

It is an object of the present invention to provide compounds which substantially inhibit the release of TNF from cells, and therefore may be used in the treatment of conditions mediated by TNF. Such uses include, but are not limited to, the treatment of inflammation, fever, cardiovascular effects, haemorrhage, coagulation and acute phase response, cachexia and anorexia, acute infections, shock states, graft versus host reactions and autoimmune disease.

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis or invasion. Several classes of MMP inhibitors have been proposed, including derivatives of hydroxamic acid. The following patent publications disclose hydroxamic acid-based MMP inhibitors, but disclose nothing concerning inhibition of TNF release:

| | |
|---|---|
| US 4599361 | (Searle) |
| EP-A-0236872 | (Roche) |
| EP-A-0274453 | (Bellon) |
| WO 90/05716 | (British Bio-technology) |
| WO 90/05719 | (British Bio-technology) |
| WO 91/02716 | (British Bio-technology) |
| EP-A-0489577 | (Celltech) |
| EP-A-0489579 | (Celltech) |
| EP-A-0497192 | (Roche) |
| WO 92/13831 | (British Bio-technology) |

The MMP inhibiting hydroxamic acid derivatives disclosed in those publications can be regarded as having the following basic structure (IA):

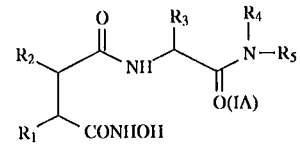

wherein the five substituents $R_1$–$R_5$ may vary according to the detailed disclosure of each publication. For compounds falling within the broad categories disclosed in those publications, the balance of intrinsic level of activity, degree of specificity of activity for a particular category of MMP, and pharmacokinetic properties can vary in an unpredictable way as the substituents $R_1$–$R_5$ are varied. Their intrinsic potency against particular MMPs can be high. For example, many have a collagenase $IC_{50}$ by the in vitro test method of Cawston and Barrett, (Anal. Biochem., 99,340–345, 1979) of less than 50 nM. Unfortunately, however, many of the specific compounds disclosed in those publications have poor water solubility, leading to severe formulation difficulties, and/or have generally poor pharmacokinetic properties. Identifying hydroxamic acid-based MMP inhibitors having a good balance of high intrinsic activity, good water solubility and acceptable pharmacokinetic properties, such that the compounds are easy to formulate and have high in vivo activity in the target disease or condition, remains a much sought after goal in the art.

It is a further object of this invention to provide compounds which, in addition to inhibiting TNF release, also inhibit the action of MMPs, and therefore may be used in the treatment of patients who suffer from conditions mediated by TNF and/or MMPs.

It is also an object of the invention to provide compounds having good water solubility and an acceptable pharmacokinetic profile.

WO-A-90 05719 (British Bio-technology), mentioned above, discloses compounds of general formula

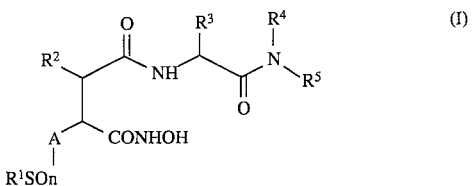

where $R^1$ represents hydrogen or an alkyl, phenyl, thienyl, substituted phenyl, phenylalkyl, heterocyclyl, alkylcarbonyl, phenacyl or substituted phenacyl group; or, when n=0, $R^1$ represents $SR^x$ wherein $R^x$ represents a group

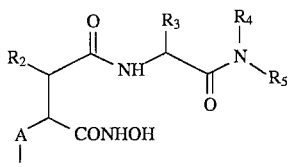

$R^2$ represents a hydrogen atom or an alkyl, alkenyl, phenylalkyl, cycloalkylalkyl or cycloalkenylalkyl group, $R^3$ represents an amino acid residue with R or S stereochemistry or an alkyl, benzyl, $(C_1-C_6$ alkoxy) benzyl or benzyloxy $(C_1-C_6$ alkyl) group; $R^4$ represents a hydrogen atom or an alkyl group; $R^5$ represents a hydrogen atom or a methyl group; n is an integer having the value 0, 1 or 2; and A represents a hydrocarbon chain optionally substituted with one or more alkyl, phenyl, or substituted phenyl groups, and their salts and N-oxides. In WO-A-90 05719 such compounds are disclosed as having collagenase inhibitory activity, with consequent utility in the management of diseases involving tissue degradation and/or the promotion of wound healing.

The compounds of the present invention differ in structure from those of WO-A-9005719 principally in the identity of the substituent $R^3$. In the compounds generically disclosed in WO-A-9005719, $R^3$ is an amino acid side chain or a $(C_1-C_6)$alkyl, benzyl, $(C_1-C_6)$alkoxybenzyl, benzyloxy $(C_1-C_6)$alkyl or benzyloxybenzyl group. However, compounds in which $R^3$ is the side chain of aspartic or glutamic acid are not specifically disclosed or their properties specifically characterised in WO-A-9005719. In the compounds of the present invention, $R^3$ represents an ester of the side chains of aspartic acid or glutamic acid, as is explained further below. Data suggests that the esters of this invention are more potent than the carboxylic acid analogues as inhibitors of TNF production.

According to the present invention there is provided a compound of formula (I):

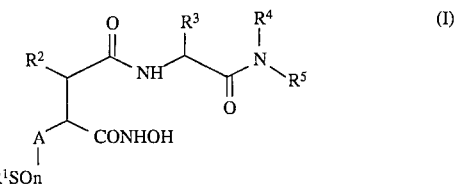

wherein:

$R^1$ represents hydrogen or an $(C_1-C_6)$alkyl, $(C_1-C_6)$alkoxycarbonyl$(C_1-C_6)$alkyl, phenyl, substituted phenyl, phenyl $(C_1-C_6)$alkyl, heterocyclyl, $(C_1-C_6)$alkylcarbonyl, phenacyl or substituted phenacyl group;

$R^2$ represents hydrogen or a $(C_1-C_6)$alkyl, $(C_2-C_6)$alkenyl, phenyl $(C_1-C_6)$alkyl, cycloalkyl $(C_1-C_6)$alkyl or cycloalkenyl $(C_1-C_6)$alkyl group;

$R^3$ represents a group —$CH_2CO_2(C_1-C_4)$alkyl or —$CH_2CH_2CO_2$ $(C_1-C_4)$alkyl;

$R^4$ represents hydrogen or a $(C_1-C_6)$alkyl or phenyl$(C_1-C_6)$alkyl group;

$R^5$ represents hydrogen or a methyl group;

n is 0, 1 or 2;

and A represents a $(C_1-C_6)$hydrocarbon chain optionally substituted with one or more $(C_1-C_6)$alkyl, phenyl, or substituted phenyl groups;

or a salt solvate or hydrate thereof.

As used herein the term "$C_1-C_6$ alkyl" refers to a straight or branched chain alkyl moiety having from 1 to 6 carbon atoms, including for example, methyl, ethyl, propyl, isopropyl, butyl, t-butyl, pentyl and hexyl.

The term "$C_2-C_6$ alkenyl" refers to a straight or branched chain alkenyl moiety having from 2 to 6 carbon atoms and having in addition one double bond of either E or Z stereochemistry where applicable. This term would include, for example, vinyl, 1-propenyl, 1- and 2-butenyl and 2-methyl-2-propenyl.

The term "cycloalkyl" refers to a saturated alicyclic moiety having from 3–6 carbon atoms and includes, for example, cyclohexyl, cyclopentyl, cyclobutyl and cyclopropyl.

The term "cycloalkenyl" refers to an alicyclic moiety having from 4–8 carbon atoms and includes, for example, cyclohexenyl, cyclopentenyl, cycloheptenyl and cyclooctenyl.

The term "heterocyclyl" refers to a 5–7 membered heterocyclic ring containing one or more heteroatoms selected from S, N and O and optionally fused to a benzene ring, including for example, pyrollyl, furanyl, thienyl, imidazolyl, oxazolyl, thiazolyl, pyrazolyl, pyridinyl, pyrrolidinyl, pyrimidinyl, morpholinyl, piperizinyl, indolyl and benzimidazolyl.

The term "substituted" as applied to any moiety means substituted with up to four substituents, each of which independently may be $C_1-C_6$ alkoxy, hydroxy, mercapto, $C_1-C_6$ alkylthio, amino, halo (including fluoro, chloro, bromo and iodo), trifluoromethyl, carboxylic acid, $C_1-C_4$ alkylcarboxy or nitro.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom adjacent the —CONHOH moiety S,
C atom adjacent the $R_2$ group—R,
C atom adjacent the $R_3$ group—S, but mixtures in which the above configurations predominate are also contemplated.

Preferred compounds of the invention include those in which, independently or in any combination:

$R^1$ represents hydrogen or an $(C_1-C_6)$alkyl, phenyl, thienyl, benzyl, acetyl, phenacyl or substituted phenyl, for example 4-hydroxy-, 4-amino- or 4-methoxyphenyl group;

$R^2$ represents a $(C_2-C_6)$alkyl group, for example a sec-butyl group;

$R^3$ represents a group —$CH_2CO_2$ $(C_1-C_4)$alkyl or —$CH_2CH_2CO_2(C_1-C_4)$alkyl, the $(C_1-C_4)$alkyl moiety being for example a methyl or tert-butyl group;

$R^4$ represents a $(C_1-C_4)$alkyl group;

$R^5$ represents a hydrogen atom;

n is 0;

A is —$CH_2$—;

or salts solvates or hydrates thereof.

Specific compounds of the invention are:

3R-(3-Methoxycarbonyl-1S-methylcarbamoyl-propylcarbamoyl)-5-methyl-2-S-phenylsulfanylmethyl hexanohydroxamic acid;

3R-(3-Methoxycarbonyl-1S-methylcarbamoyl-propylcarbamoyl)-5-methyl-2S-(thien-2-ylsulfanylmethyl)-hexanohydroxamic acid;

2S-(4-Methoxy-phenylsulfanylmethyl)-3R-(3-methoxycarbonyl-1S-methylcarbamoyl-propylcarbamoyl)- 5-methyl-hexanohydroxamic acid;

2S-(4-Amino-phenylsulfanylmethyl)-3R-(3-methoxycarbonyl-1S-methylcarbamoyl-propylcarbamoyl)- 5-methyl-hexanohydroxamic acid;

2S-(Ethylsulfanylmethyl)-3R-(3-methoxycarbonyl-1S-methylcarbamoyl-propylcarbamoyl)-5-methyl-hexanohydroxamic acid;

2S-(Acetylsulfanylmethyl)-3R-(3-methoxycarbonyl-1S-methylcarbamoyl-propylcarbamoyl)-5-methyl-hexanohydroxamic acid;

2S-(Benzylsulfanylmethyl)-3R-(3-methoxycarbonyl-1S-methylcarbamoyl-propylcarbamoyl)- 5-methyl-hexanohydroxamic acid;

2S-(tert-Butylsulfanylmethyl)-3R-(3-methoxycarbonyl-1S-methylcarbamoyl-propylcarbamoyl)- 5-methyl-hexanohydroxamic acid;

2S-Thiomethyl-3R-(3-methoxycarbonyl-1S-methylcarbamoyl-propylcarbamoyl)-5-methyl-hexanohydroxamic acid;

2S-(4-Hydroxyphenylsulfanylmethyl)-3R-(2-tert-butoxycarbonyl-1S-methylcarbamoyl-phenylsulphinylmethyl)- 5-methyl-hexanohydroxamic acid;

2S-(4-Hydroxy-phenylsulphinylmethyl)-3R-(3-methoxycarbonyl-1S-methylcarbamoyl-propylcarbamoyl)- 5-methyl-hexanohydroxamic acid;

2S-(4-Hydroxy-phenylsulphonylmethyl)-3R-(3-methoxycarbonyl-1S-methylcarbamoyl-propylcarbamoyl)- 5-methyl-hexanohydroxamic acid;

and salts, hydrates and solvates thereof.

Compounds of the invention which are presently particularly preferred, inter alia for their potency in inhibiting TNF release, and their water solubility are:

2S-(4-Hydroxyphenylsulfanylmethyl)-3R-(3-methoxycarbonyl-1S-methylcarbamoyl-propylcarbamoyl)- 5-methyl-hexanohydroxamic acid;

2S-(4-Hydroxyphenylsulfanylmethyl)-3R-(3-tert butoxycarbonyl-1S-methylcarbamoyl-propylcarbamoyl)- 5-methyl-hexanohydroxamic acid;

and salts (for example the hydrochloride), hydrates and solvates thereof.

Compounds of general formula (I) may be prepared by any suitable method known in the art and/or by the following process, which itself forms part of the invention, namely a process for preparing a compound of general formula (I) as defined above, comprising:

(a) coupling an acid of general formula (II)

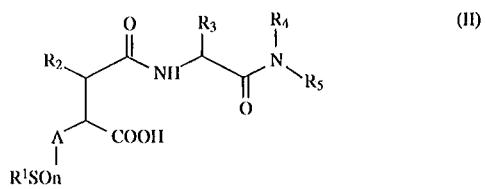

or an activated derivative thereof with hydroxylamine, O-protected hydroxylamine, or a salt thereof, $R^1$, $R^2$, $R^3$, $R^4$, $R^5$, A and n being as defined in general formula (I) except that any substituents in $R^1$, $R^2$, $R^3$, and A which are potentially reactive with hydroxylamine, O-protected hydroxylamine or their salts may themselves be protected from such reaction, then removing any protecting groups from the resultant hydroxamic acid moiety and from any protected substituents in $R^1$, $R^2$, $R^3$ and A; or (b) esterifying a compound of formula (IIA)

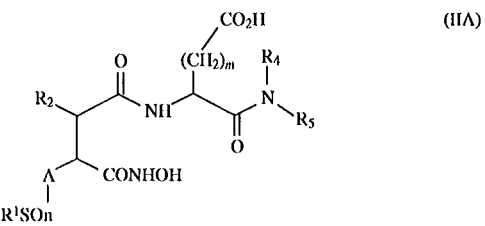

wherein m=1 or 2 and $R^1$, $R^2$, $R^4$, $R^5$ and A are as defined in formula (I), with an alcohol of formula $HO(C_1-C_4)$alkyl; and (c) optionally after step (a) or (b) convening a compound of general formula (I) into another compound of general formula (I).

Compounds of general formula (I) which are sulphoxides or sulphones can be prepared from sulphanyl compounds of general formula (I) (n=0) by oxidation.

Conversion of (II) to an activated intermediate such as the pentafluorophenyl, hydroxysuccinyl, or hydroxybenztriazyl ester may be effected by reaction with the appropriate alcohol in the presence of a dehydrating agent such as dicyclohexyl dicarbodiimide (DCC), N,N-dimethylaminopropyl-N'-ethyl carbodiimide (WSCDI), or 2-ethoxy-1-ethoxycarbonyl-1,2-dihydroquinoline (EEDQ). Esterification of (IIA) may be effected by standard methods.

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl, t-butyldimethylsilyl, tetrahydropyranyl or benzyl ether, or as readily cleavable esters such as the acetate. Carboxy groups are often protectable as readily cleavable esters, such as the t-butyl or benzyl ester.

A compound of formula (II) may be prepared by de-esterification (such as by hydrolysis) of an ester of formula (IV)

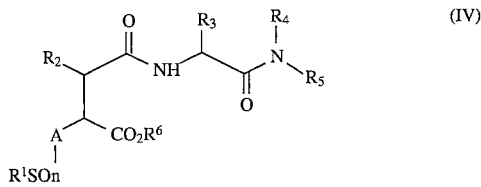

wherein $R^1$, $R^2$, $R^3$, $R^4$, $R^5$, A and n are as defined in general formula (I) and $R^6$ represents $C_1$–$C_6$ alkyl, 2-trimethylsilylethyl, phenyl $C_1$–$C_6$ alkyl or substituted phenyl $C_1$–$C_6$ alkyl.

A compound of formula (IV) can be prepared from an ester of formula (V) or an acid of formula (VI)

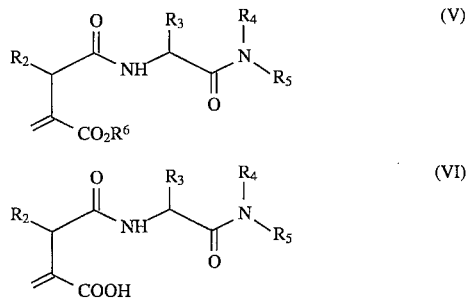

wherein $R^2$, $R^3$, $R^4$, and $R^5$, are as defined in general formula (I) and $R^6$ represents $C_1$–$C_6$ alkyl, phenyl $C_1$–$C_6$ alkyl or substituted phenyl $C_1$–$C_6$ alkyl, by reaction with a thiol $R^1$SH, wherein $R^1$ is as defined in formula (I), to give compounds wherein A represents a methylene group, or by reaction with a cuprate of formula $(R^1—S—A^1)_2$CuLi wherein $R^1$ is as defined in formula (I), and $A^1$ is such that —$A^1$—$CH_2$— is identical to —A— as defined in formula (I).

Esters of formula (V) can be prepared by esterifying acids of formula (VI) with an appropriate alcohol $R^6$OH or other esterifying agent.

An acid of formula (VI) can be prepared by reacting a malonic acid derivative of formula (VII)

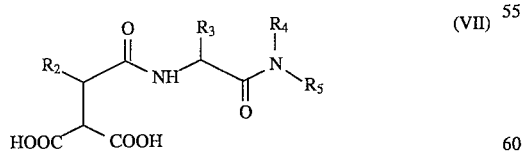

wherein $R^2$, $R^3$, $R^4$, and $R^5$, are as defined in general formula (I), with formaldehyde in the presence of piperidine.

An acid of general formula (VII) can in turn be prepared by de-esterifying (for example by hydrolysis) a compound of formula (VIII)

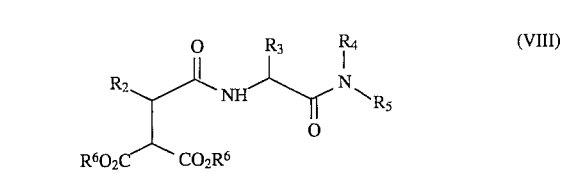

wherein $R^2$, $R^3$, $R^4$, and $R^5$ are as defined in general formula (I) and $R^6$ represents $C_1$–$C_6$ alkyl, phenyl $C_1$–$C_6$ alkyl or substituted phenyl $C_1$–$C_6$ alkyl.

A compound of general formula (VIII) can be prepared by coupling a compound of formula (IX) with a compound of formula (X)

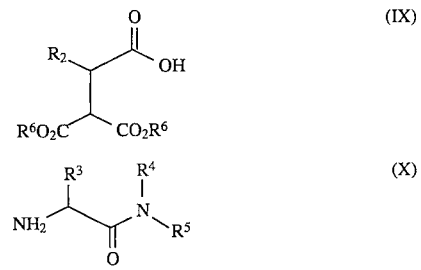

wherein $R^2$, $R^3$, $R^4$, and $R^5$ are as defined in general formula (I) and $R^6$ represents $C_1$–$C_6$ alkyl, phenyl $C_1$–$C_6$ alkyl or substituted phenyl $C_1$–$C_6$ alkyl.

The starting materials and other reagents are either available commercially or can be synthesised by simple chemical procedures.

For example, a substituted acid of formula (IX) may be prepared by reacting an ester of formula (XI)

wherein Y represents halo and $R^2$ and $R^6$ are as defined above, with a malonate derivative of formula (XII)

wherein $R^6$ is as defined above, with the proviso that when $R^6$ is benzylic in formula (XI) it is aliphatic in formula (XII), or vice versa, and selectively deesterifying.

Compounds of general formula (XI) can simply be derived from amino acids, which can be obtained in enantiomerically pure form, enabling a choice of optically active compounds of formula (I) to be prepared.

Compounds of formula (II) and (IIA) are valuable intermediates in the preparation of compounds of formula (I), and in that respect form part of the present invention.

As mentioned above, compounds of formula (I) are useful in human or veterinary medicine since they are active as inhibitors of TNF and MMPs. Accordingly in another aspect, this invention concerns:

(i) a method of management (by which is meant treatment or prophylaxis) of diseases or conditions mediated by TNF and/or MMPs in mammals, in particular in humans, which method comprises administering to the mammal an effective, amount of a compound of formula (I) above, or a pharmaceutically acceptable salt thereof; and (ii) a compound of formula (I) for use in human or veterinary medicine, particularly in the management (by which is meant treatment or prophylaxis) of diseases or conditions mediated by TNF and/or MMPs; and (iii) the use of a compound of formula (I) in the preparation of an agent for the management (by which is meant treatment or prophylaxis) of diseases or conditions mediated by TNF and/or MMPs.

The diseases or conditions referred to above include inflammation, fever, cardiovascular effects, haemorrhage, coagulation and acute phase response, cachexia and anorexia, acute infections, shock states, graft versus host reactions and autoimmune disease; and those involving tissue breakdown such as bone resorption, inflammatory diseases, dermatological conditions, tumour growth, angiogenesis and invasion by secondary metastases, in particular rheumatoid arthritis, osteoarthritis, periodontitis, gingivitis, corneal ulceration, tumour growth, angiogenesis and invasion by secondary metastases.

In a further aspect of the invention there is provided a pharmaceutical or veterinary composition comprising a compound of formula (I) together with a pharmaceutically or veterinarily acceptable excipient or carrier.

One or more compounds of general formula (I) may be present in the composition together with one or more excipient or carrier.

The compounds with which the invention is concerned may be prepared for administration by any route consistent with their physicochemical and pharmacokinetic properties. The compositions thus may be in the form of tablets, capsules, powders, granules, lozenges, liquid or gel preparations, such as oral, topical, or sterile parenteral solutions or suspensions, as appropriate. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit for oral administration may contain from about 1 to 250 mg, for example from about 25 to 250 mg of a compound of general formula I. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The following examples 1–14 illustrate the invention in more detail, but are not intended to limit the scope in any way. Biological Examples A–C illustrate the activity of some of the compounds of the invention. The comparative example describes the preparation of a compound related in structure to those of the invention, said comparative compound being an example of the class of intermediates of formula (IIA) above for the preparation of compounds of the invention.

| Abbreviations | |
|---|---|
| WSCDI | N,N-dimethylaminopropyl-N'-ethyl carbodiimide |
| DMF | N,N-dimethylformamide |
| NMM | N-methylmorpholine |
| DCM | Dichloromethane |
| HOBT | Hydroxybenztriazole |

EXAMPLE 1

3R-(3-Methoxycarbonyl-1S-methylcarbamoyl-propylcarbamoyl)-5-methyl-2-S-phenylsulfanylmethyl hexanohydroxamic acid.

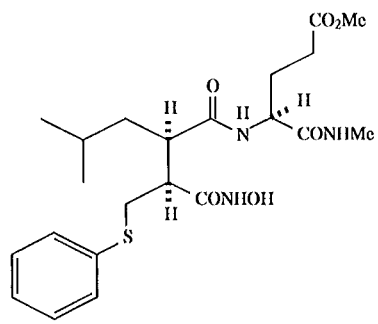

a) N-Methyl-4-methoxycarbonyl-2S-aminobutanamide trifluoroacetic acid salt (12.55 g, 72 mmol) was taken up in DMF and stirred at 0° C., 2-benzyloxycarbonyl-3R-isobutyl succinic acid-4-pentafluorophenyl-1-benzyl diester (56.98 g, 143.8 mmol) and N-methyl morpholine (31.56 g, 312 mmol) were added and the mixture gradually allowed to warm to room temperature and stirred overnight. Solvent was removed under vacuum and the residue taken up in DCM then washed with 1M sodium carbonate, 1M hydrochloric acid and brine, then dried over magnesuim sulphate. Solvent was removed under vacuum and the crude product purified by column chomatography (silica gel, DCM). The product was then further purified by column chromatography (silica gel, DCM/ethyl acetate, 1:1) to provide a white solid.

The title compound was recrystallized from ethyl acetate/hexane (12.01 g, 21.65 mmol, 30%):$^1$H-NMR; δ (CDCl$_3$), 7.29 (10H, m, Aryl-H), 6.82 (1H, d, J=7.4 Hz, CONH̲CH), 6.43 (1H, q, J=4.5 Hz, CNH̲CH$_3$), 5.11 (4H, m, CH̲$_2$Ph), 4.36 (1H, m, NHCH̲CO), 3.81 (1H, d, J=9.8 Hz, CH̲(CO$_2$Bn)$_2$), 3.65 (3H, s, CO$_2$CH̲$_3$), 2.96 (1H, dt, J=3.9 Hz, $^i$BuCH̲), 2.78 (3H, d, J=4.8 Hz, NHCH̲$_3$), 2.49 (1H, m, CH$_2$CH̲$_2$CO$_2$CH$_3$), 2.35 (1H, m, CH$_2$CH̲$_2$CO$_2$CH$_3$) CH̲$_2$CH$_2$CO$_2$CH$_3$), 1.92 (1H, m, CH̲$_2$CH$_2$CO$_2$CH$_3$), 1.60 (2H, m, (CH$_3$)$_2$CHCH̲$_2$), 1.04 (1H, m, CH(CH$_3$)$_2$), 0.82 (6H, 2×d, J=5.8 Hz, CH(CH̲$_3$)$_2$).

b) 2-[1R-(3-Methoxycarbonyl-1S-methylcarbamoyl-propylcarbamoyl)-3-methyl-butyl]-acrylic acid.

2-[1R-(3-Methoxycarbonyl-1S-methylcarbamoyl-propylcarbamoyl)-3-methyl-butyl]-malonic acid dibenzyl ester (12.01 g, 21.65 mmol) was dissolved in ethanol (200 ml), 20% palladium on charcoal (2.4 g) added and the mixture subjected to an atmosphere of hydrogen for 1.5 hours. The catalyst was removed by filtration and the solvent removed under vacuum to give the diacid as a white solid (about 8.5 g). This crude diacid was taken up in ethanol (250 ml) and piperidine (2.03 g, 23.81 mmol) was added. After 15 minutes the solution was cooled to 0° C and formaldehyde (37% aqueous solution, 16.2 ml, 216 mmol) was added. The reaction stirred at room temperature overnight. Solvent was removed under vacuum and the residue taken up in ethyl acetate and washed with 1M hydrochloric acid then brine. The organic layer was separated and dried over magnesuim sulphate then the solvent was removed to give the title compound as a white solid (3.89, 11.37 mmol, 53%): $^1$H-NMR, δ (CDCl$_3$), 8.10 (1H, d, J=8.8 Hz, CONH̲CH), 7.10 (1H, q, J=4.8 Hz, CONH̲CH$_3$), 6.47 (1H, s, CH̲$_2$=C), 5.95 (1H, s, CH̲$_2$=C), 4.65 (1H, m, NHCH̲CO), 3.79 (1H, t, J=6.9 Hz, $^i$BuCH̲), 3.63 (3H, s, CO$_2$CH̲$_3$), 2.84 (3H, d, J=4.7 Hz, NHCH̲$_3$), 2.32 (2H, m, CH$_2$CH̲$_2$CO$_2$CH$_3$), 2.01 (1H, m, CH̲$_2$CH$_2$CO$_2$CH$_3$), 1.90 (1H, m, CH̲CH$_2$CH$_2$CO$_2$CH$_3$), 1.78 (1H, m, (CH$_3$)$_2$CHCH̲$_2$), 1.51 (2H, m, (CH$_3$)$_2$CHCH̲$_2$ and (CH$_3$)$_2$CHCH̲$_2$), and 0.87 (6H, 2×d, J=6.2 Hz, CH(CH̲$_3$)$_2$).

c) 3R-(3-Methoxycarbonyl-1S-methylcarbamoyl-propylcarbamoyl)-5-methyl-2-S-phenylsulfanylmethyl hexanoic acid.

2-[1R-(3-Methoxycarbonyl-1S-methylcarbamoyl-propylcarbamoyl)-3-methyl-butyl]-acrylic acid (0.2 g, 0.58 mmol) was taken up in thiophenol (5 ml) and the mixture heated at 60° C. under argon with the exclusion of light overnight. Crude product was purified by column chromatography (silica gel, hexane then ethyl acetate) to provide the title compound as a white solid (37 mg, 0.08 mmol, 14%): $^1$H-NMR; δ (CDCl$_3$), 7.96 (1H, d, J=7.8 Hz, CONH̲CH), 7.27 (5H, m, aryl-H), 6.79 (1H, q, J=4.8 Hz, CONH̲CH$_3$), 4.54 (1H, m, NHCH̲CO), 3.64 (3H, s, CO$_2$CH̲$_3$), 3.30 (1H, dd, J=13.2, 8.3 Hz, CHCH̲$_2$S), 3.02 (1H, dd, J=13.0, 5.5 Hz, CHCH̲$_2$S), 2.81 (5H, m, $^i$BuCH, CH̲CH$_2$S and CONHCH̲$_3$), 2.42 (1H, m, CH$_2$CH̲$_2$CO$_2$CH$_3$), 2.11 (1H, m, CH̲$_2$CH$_2$CO$_2$CH$_3$), 1.97 (1H, m, CH̲$_2$CH$_2$CO$_2$CH$_3$), 1.74 (1H, m, (CH$_3$)2CHCH̲$_2$), 1.39 (1H, m, (CH$_3$)$_2$CHCH̲$_2$), 1.17 (1H, m, (CH$_3$)$_2$CHCH̲$_2$), and 0.84 (6H, d, J=6.4 Hz, (CH̲$_3$)$_2$CHCH$_2$) $^{13}$C-NMR; (CDCl$_3$), 174.6, 173.1, 171.9, 171.2, 133.8, 128.2, 127.6, 125.0, 50.7, 50.4, 46.4, 45.0, 38.4, 32.5, 28.6, 25.7, 25.0, 24.5, 22.2, and 19.0.

d) 3R-(3-Methoxycarbonyl-1S-methylcarbamoyl-propylcarbamoyl)-5-methyl-2-S-phenylsulfanylmethyl hexanohydroxamic acid. 3R-(3-Methoxycarbonyl-1S-methylcarbamoyl-propylcarbamoyl)-5-methyl-2-S-phenylsulfanylmethyl hexanoic acid (37 mg, 0.082 mmol) was taken up in DCM and cooled to 0° C. while HOBT (14.3 mg, 0.106 mmol), NMM (10.6 mg, 0.106 mmol) and N-(dimethylaminoethyl)-N'-ethylcarbodiimide (WSCDI, 20.3 mg, 0.106 mmol) were added. The reaction was stirred at 0° C. while hydroxylamine hydrochloride (9.2 mg, 0.132 mmol) and NMM (13.3 mg, 0.132 mmol) were added and the reaction stirred at room temperature for two days. Solvent was removed under vacuum and the residue partitioned between diethyl ether/water and the title compound collected by filtration as a white solid (19.2 mg, 0.041 mmol, 50%): $^1$H-NMR; δ (methanol-d$_4$), 7.24 (5H, m, Aryl-H), 4.34 (1H, m, NHCH̲CO), 3.56 (3H, s, CO$_2$CH̲$_3$), 2.98 (2H, m, CH̲CH$_2$S), 2.69 (3H, s, CONHCH̲$_3$), 2.58 (1H, m, $^i$BuCH̲), 2.38 (3H, m, CH̲CH$_2$S and CH$_2$CH̲$_2$CO$_2$CH$_3$), 1.95 (2H, m, CH̲$_2$CH$_2$CO$_2$CH$_3$), 1.51 (2H, m, (CH$_3$)$_2$CHCH̲$_2$), 1.04 (1H, m, (CH$_3$)$_2$CHCH̲$_2$), 0.86 (3H, d, J=6.4 Hz, CH(CH̲$_3$)$_2$), and 0.80 (3H, d, J=6.4 Hz, CH(CH̲$_3$)$_2$): $^{13}$C NMR;δ (methanol-d$_4$), 176.1, 174.6, 173.5, 171.4, 130.1, 129.6, 129.6, 53.8, 53.2, 41.6, 35.0, 31.1, 28.1, 26.8, 25.2, 24.5, and 22.2.

EXAMPLE 2

3R-(3-Methoxycarbonyl-1S-methylcarbamoyl-propylcarbamoyl)-5-methyl-2S-(thien-2-ylsulfanylmethyl)-hexanohydroxamic acid.

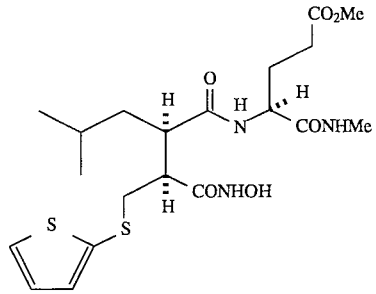

a) 3R-(3-Methoxycarbonyl-1S-methylcarbamoyl-propylcarbamoyl)-5-methyl-2S-(thien-2-ylsulfanylmethyl)-hexanoic acid.

3R-(3-Methoxycarbonyl-1S-methylcarbamoyl-propylcarbamoyl)-3-methyl-butyl]-acrylic acid (1.18 g, 3.47 mmol) was treated with thiophene-2-thiol as described in example 1c. Crude product was purified by column chromatography (silica gel, DCM then 10% MeOH/DCM) to provide the title compound as a white solid (1.21 g, 2.64 mmol, 76%): $^1$H-NMR ,δ (methanol-d$_4$), 7.41 (1H, m, thienyl-H5), 7.12 (1H, m, thienyl-H3), 6.94 (1H, m, thienyl-H4), 4.27 (1H, m, NHCH̲CO), 3.63 (3H, s, CO$_2$CH̲$_3$), 2.94 (2H, m, CHCH̲$_2$S), 2.69 (5H, m, CONHCH̲$_3$ and $^i$BuCH̲ and CH̲CH$_2$S), 2.36 (2H, m, CH$_2$CH̲$_2$CO$_2$CH$_3$), 1.61 (1H, m, (CH$_3$)$_2$CHCH̲$_2$), 1.39 (1H, m, (CH$_3$)$_2$CH̲CH$_2$), 1.10 (1H, m, (CH$_3$)$_2$CHCH̲$_2$), 0.88 (3H, d, J=6.6 Hz, CH(CH̲$_3$)$_2$), and 0.79 (3H, d, J=6.5 Hz, CH(CH̲$_3$)$_2$).

b) 3R-(3-Methoxycarbonyl-1S-methylcarbamoyl-propylcarbamoyl)-5-methyl-2S-(thien-2-ylsulfanylmethyl)- hexanohydroxamic acid 3R-(3-Methoxycarbonyl-1S-methylcarbamoyl-propylcarbamoyl)-5-methyl-2S-(thien- 2-ylsulfanylmethyl)-hexanoic acid (1.0 g, 2.2 mmol) was coupled with hydroxylamine as described in example 1 d to produce the title compound which was purified by column chromatography (acid washed silica gel, 10% MeOH/DCM) then triturated with diethyl ether to provide a white solid (170 mg, 0.4 mmol, 17%): $^1$H-NMR; δ (methanol-d$_4$), 7.4 (1H, d, J=5.3 Hz, thienyl-H5), 7.1 (1H, d, J=2.5 Hz, thienyl-H3), 6.94 (1H, m, thienyl-H4), 4.26 (1H, m, NHC HCO), 3.63 (3H, s, CO$_2$CH$_3$), 2.96 (1H, dd, J=12.9, 11.2 Hz, CHCH$_2$S), 2.75 (1H, dd, J=12.8, 3.4 Hz, CHC H$_2$S), 2.67 (3H, s, CONHCH$_3$), 2.55 (1H, dd, J=10.9, 3.1 Hz, CHCH$_2$S), 2.37 (3H, m, $^t$BuCH and CH$_2$CH H$_2$CO$_2$CH$_3$), 1.92 (2H, m, CH$_2$CH$_2$CO$_2$CH$_3$), 1.50 (1H, m, (CH$_3$)2CHCH$_2$), 1.34 (1H, m, (CH$_3$)$_2$C HCH$_2$), 1.05 (1H, m, (CH$_3$)$_2$CHCH$_2$), and 0.80 (6H, 2xd, J=6.6, 6.5 Hz, CH(CH$_3$)$_2$).

EXAMPLE 3

2S-(4-Hydroxyphenylsulfanylmethyl)-3R-(3-methoxycarbonyl-1S-methylcarbamoyl-propylcarbamoyl)- 5-methyl-hexanohydroxamic acid.

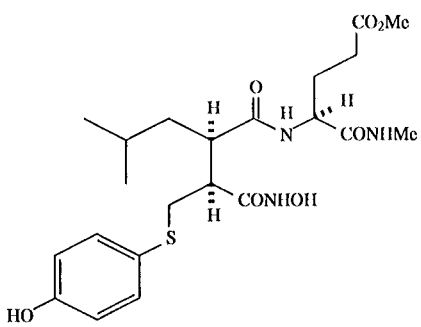

a) 2S-(4-Hydroxyphenylsulfanylmethyl)-3R-(3-methoxycarbonyl-1S-methylcarbamoyl-propylcarbamoyl)-5-methyl-hexanoic acid. 2-[1R-(3-Methoxycarbonyl-1S-methylcarbamoyl-propylcarbamoyl)-3-methyl-butyl]-acrylic acid (2.18 g, 6.37 mmol) was taken up in methanol (10 ml) and 4-hydroxythiophenol (5 ml) added then the mixture stirred at reflux under argon over night. Solvent removal gave a yellow solid which was purified by column chromatography (silica gel, 0–10% methanol/DCM) to give the title compound as a yellow foam (2.02 g, 4.32 mmol, 68%): $^1$H-NMR; δ (methanol-d$_4$), 7.19 (2H, d, J=8.7 Hz, Aryl-H), 6.69 (2H, d, J=8.7 Hz, Aryl-H), 4.29 (1H, m, COCHNH), 3.62 (3H, s, CO$_2$CHH$_3$), 2.96 (1H, m, CHCH$_2$S), 2.81 (1H, m, CHCH$_2$S), 2.69 (3H, s, NHCH$_3$), 2.61 (1H, m, CH), 2.33 (3H, m, CH$_2$CH$_2$CO$_2$CH$_3$ and CHCH$_2$S), 2.04 (2H, m, CH$_2$CH$_2$CO$_2$CH$_3$), 1.65 (1H, m, (CH$_3$)$_2$CHCH$_2$), 0.85 (3H, d, J=6.5 Hz, CH(CH$_3$)$_2$), and 0.79 (3H, d, J=6.6 Hz, CH(CH$_3$)$_2$).

b) 2S-(4-Hydroxyphenylsulfanylmethyl)-3R-(3-methoxycarbonyl-1S-methylcarbamoyl-propylcarbamoyl)-5-methyl-hexanohydroxamic acid. 2S-(4-Hydroxyphenylsulfanylmethyl)-3R-(3-methoxycarbonyl-1S-methylcarbamoyl-propylcarbamoyl)- 5-methyl-hexanoic acid (1.18 g, 2.5 mmol) was taken up in DCM and a small amount of DMF added. The solution was cooled to 0° C. while pentafluorophenol (0.93, 5 mmol), NMM (0.3 g, 3 mmol) and WSCDI (0.58 g, 3 mmol) were added. The reaction was stirred at 0° C. for 2 hours then room temperature for 1 hour. Solvent was removed under reduced pressure and the residue taken up in DCM then washed with 2M hydrochloric acid, saturated soduim bicarbonate soluton and brine, then dried over magnesuim sulphate. Solvent was removed under reduced pressure and the residue taken up in DCM, to which hydroxylamine hydrochloride (0.23 g, 3.25 mmol) and NMM (0.33 g, 3.25 mmol) were added and the reaction stirred at room temperature over night. The resulting precipitate was collected by filtration, washed with water and dried under reduced pressure to provide 2S-(4-hydroxy-phenylsulfanylmethyl)- 3R-(3-methoxycarbonyl-1S-methylcarbamoyl-propylcarbamoyl)-5-methyl-hexanohydroxamic acid as a white solid (0.56 g, 1.16 mmol, 46%): $^1$H-NMR, δ (methanol-d$_4$), 7.18 (2H, d, J=8.6 Hz, Aryl-H), 6.68 (2H, d, J=8.6 Hz, Aryl-H), 4.29 (1H, dd, J=5.6, 5.4 Hz, COCHNH), 3.62 (3H, s, CO$_2$CH$_3$) 2.89 (1H, m, CHCH$_2$S), 2.76 (1H, dd, J=12.9, 3.6 Hz, CHCH$_2$S), 2.67 (3H, s, NHCH$_3$), 2.55 (1H, m, $^t$BuCH), 2.34 (3H, m, CH$_2$CH$_2$CO$_2$CH$_3$ and C HCH$_2$S), 1.97 (2H, m, CH$_2$CH$_2$CO$_2$CH$_3$), 1.48 (2H, m, (CH$_3$)$_2$CHCH$_2$), 1.01 (1H, m, (CH$_3$)$_2$ CHCH$_2$), 0.83 (3H, d, J=6.4 Hz, CH(CH$_3$)$_2$), and 0.79 (3H, d, J=6.5 Hz, CH(CH$_3$)$_2$): $^{13}$C-NMR;δ (methanol-d$_4$) 175.9, 174.7, 173.7, 171.3, 158.2, 134.3, 125.6, 117.1, 53.7, 52.2, 41.5, 37.4, 31.1,28.1,26.8, 26.2, 24.3, and 21.6.

The mother liquor was purified by column chromatography (acid washed silica gel, 10% methanol/DCM) and recrystallization of the resultant white solid from methanol/ diisopropyl ether provided 2R-(4-Hydroxy-phenylsulfanylmethyl)- 3R-(3-methoxycarbonyl-1S-methylcarbamoyl-propylcarbamoyl)- 5-methyl-hexanohydroxamic acid as the minor diastereoisomer: Analysis for C$_{22}$H$_{33}$N$_3$O$_7$S; requires C 54.64, H 6.88, N 8.70: Found C 53.79H 6.78N 8.54: $^1$H-NMR; (methanol-d$_4$), 7.17 (2H, d, J=8.7 Hz, Aryl-H), 4.22 (1H, dd, J=9.6, 5.3 Hz, NHCHCO), 3.62 (3H, s, CO$_2$C H$_3$), 2.99 (1H, dd, J=13.4, 3.6 Hz, CHCH$_2$S), 2.87 (1H, m, CHCH$_2$S), 2.67 (3H, s, NHCH$_3$), 2.55 (1H,m, $^t$BuCH), 2.33 (3H, m, CHCH$_2$S and CH$_2$CH$_2$CO$_2$CH$_3$), 2.06 (1H, m, CH$_2$CH$_2$CO$_2$CH$_3$), 1.85 (1H, m, CH$_2$CH$_2$CO$_2$CH$_3$), 1.51 (1H,m, (CH$_3$)$_2$CHCH$_2$), 0.84 (3H, d, J=7.1 Hz, CH(C H$_3$)$_2$), 0.79 (3H, d, J=6.9 Hz, CH(CH$_3$)$_2$); 13C-NMR; (methanol-d$_4$), 172.1, 171.2, 168.0, 155.7, 130.8, 123.7, 115.4, 51.41, 50.9, 45.8, 45.4, 33.9, 29.4, 26.1,25.0, 23.5, 20.7.

EXAMPLE 4

2S-(4-Methoxy-phenylsulfanylmethyl)-3R-(3-methoxycarbonyl-1S-methylcarbamoyl-propylcarbamoyl)- 5-methyl-hexanohydroxamio acid.

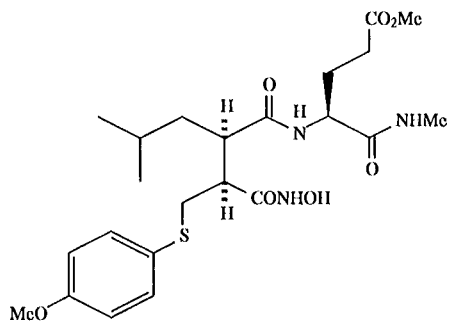

a) 2S-(4-Methoxy-phenylsulfanylmethyl)-3R-(3-methoxycarbonyl-1S-methylcarbamoyl-propylcarbamoyl)-5-methyl-hexanoic acid.

p-Methoxythiophenol (4 ml) and methanol (2 ml) were added to 2-[1R-(3-methoxycarbonyl- 1S-methylcarbamoyl)-3-methylbutyl]-acrylic acid (1.01 g, 2.9 mmol) and the mixture stirred for 2 days in the dark at 60° C., under argon. Diethyl ether (30 ml) was added to the mixture and resulting white precipitate filtered and thoroughly washed in cold ether to provide the title compound (0.88 g, 1.8 mmole, 62%); $^1$H NMR $\delta_H$; (Methanol-$d_4$), 7.30 (2H, d, J=8.7 Hz, Ar—H), 6.82 (2H, d, J=8.8 Hz, Ar—H), 4.29 (1H, dd, J=5.7, 8.7 Hz, CHCH$_2$CH$_2$), 3.74 (3H, s, COCH$_3$), 3.62 (3H, s, CO$_2$CH$_3$), 2.87 (2H, m, CHCH$_2$S), 2.67 (3H, s, CONHCH$_3$), 2.64 (2H, m, CHCHCH$_2$S), 2.33 (2H, m, CH$_2$CH$_2$CO$_2$CH$_3$), 2.09–1.79 (2H, bm, CH$_2$CH$_2$CO$_2$CH$_3$), 1.57 (1H, m, (CH$_3$)$_2$CHCH$_2$), 1.36 (1H, m, (CH$_3$)$_2$CHCH$_2$), 1.07 (1H, m, (CH$_3$)2 CHCH$_2$), 0.83 (3H, d, J=6.5 Hz, (CH$_3$)$_2$CH) and 0.79 (3H, d, J=6.5 Hz, (CH$_3$)$_2$CH).

b) 2S-(4-Methoxy-phenylsulfanylmethyl)-3R-(3-methoxycarbonyl-1S-methylcarbamoyl-propylcarbamoyl)-5-methyl-hexanohydroxamic acid. 2S-(4-Methoxy-phenylsulfanylmethyl)-3R-(3-methoxycarbonyl-1S-methylcarbamoyl-propylcarbamoyl)- 5-methyl-hexanoic acid (0.88 g, 1.8 mmol) was taken up in DMF (5 ml) and stirred in an ice bath. HOBT (0.28 g, 2.1 mmol) and WSCDI (0.40 g, 2.1 mmol) were added and the mixture stirred for about 30 minutes in the ice bath followed by 2 hours at room temperature. The mixture was once again cooled in an ice bath and hydroxylamine hydrochloride (0.18 g, 2.6 mmol) and NMM (0.26 g, 2.6 mmol) added, before stirring at room temperature overnight. DMF was removed under high vacuum and the residue slurried in ether/H$_2$O (1:1, 50 ml). The resulting white precipitate was filtered and thoroughly washed with ether and water, before drying in-vacuo (0.45 g, 0.9 mmol, 52%). m.p. 188°–189° C.; $^1$H-NMR $\delta_H$; (Methanol-$d_4$), 7.26 (2H, d, J=8.8 Hz, Ar—H), 6.82 (2H, d, J=8.9 Hz, Ar—H), 4.31 (1H, dd, J=5.6, 8.7 Hz, CHCH$_2$CH$_2$), 3.74 (3H, s, COCH$_3$), 3.60 (3H, CO$_2$CH$_3$), 2.96 (1H, dd, J=11.3, 12.9 Hz, CHCHCH$_2$S), 2.80 (1H, dd, J=3.6, 13.0 Hz, CHCHCH$_2$S), 2.68 (3H, s, CONHCH$_3$), 2.57 (1H, dt, J=3.5, 10.8 Hz, CHCHCH$_2$S), 2.36 (3H, m, CH$_2$CH$_2$CO$_2$CH$_3$+CHCHCH$_2$S), 2.09–1.79 (2H, bm, CH$_2$CH$_2$CO$_2$CH$_3$), 1.51 (1H, m, (CH$_3$)$_2$CHCH$_2$), 1.38 (1H, m, (CH$_3$)$_2$CHCH$_2$), 1.05 (1H, m, (CH$_3$)$_2$CHCH$_2$), 0.84 (3H, d, J=6.4 Hz, (CH$_3$)$_2$CH) and 0.79 (3H, d, J=6.6 Hz, (CH$_3$)$_2$CH); $^{13}$C-NMR; $\delta_C$(Methanol-$d_4$), 175.9, 174.7, 173.7, 171.3, 160.6, 133.8, 127.5, 115.8, 55.8, 53.8, 52.2, 48.2, 37.1,31.2, 28.2, 26.9, 24.3 and 21.7.

EXAMPLE 5

2S-(4-Amino-phenylsulfanylmethyl)-3 R-(3-methoxycarbonyl-1S-methylcarbamoyl-propylcarbamoyl)- 5-methyl-hexanohydroxamic acid.

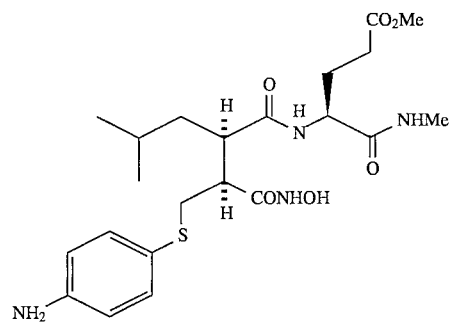

a) 2S-(4-Amino-phenylsulfanylmethyl)-3R-(3-methoxycarbonyl-1S-methylcarbamoyl-propylcarbamoyl)-5-methyl-hexanoic acid.

p-Aminothiophenol (4 ml) and methanol (3 ml) were added to 2-[1R-(3-methoxycarbonyl- 1S-methylcarbamoyl)-3-methylbutyl]-acrylic acid (0.78 g, 2.3 mmol) and the mixture stirred overnight in the dark at 60° C., under argon. The mixture was purified by column chromatography (silica gel, 2–10% methanol/DCM) to give a white solid which was further purified by recrystallisation from EtOAc/EtOH/hexane (0.52 g, 1.1 mmole, 49%); $^1$H-NMR $\delta_H$; (Methanol-$d_4$), 7.14 (2H, d, J=6.5 Hz, Ar—H), 6.60 (2H, d, J=6.7 Hz, Ar—H), 4.27 (1H, dd, J=5.6, 8.7 Hz, CHCH$_2$CH$_2$), 3.63 (3H, s, CO$_2$CHH$_3$), 2.80 (2H, m, CHCHCHH$_2$S), 2.66 (3H, s, CONHCH$_3$), 2.68–2.52 (2H, bm, CHCHCH$_2$S), 2.35 (2H, m, CH$_2$CH$_2$CO$_2$CH$_3$), 2.08–1.76 (2H, bm, CH$_2$CH$_2$CO$_2$CH$_3$), 1.57 (1H, m, (CH$_3$)2CHCH$_2$), 1.35 (1H, m, (CH$_3$)2CHCH$_2$), 1.04 (1H, m, (CH$_3$)$_2$CHCH$_2$), 0.83 (3H, d, J=6.4 Hz, (CH$_3$)$_2$CH) and 0.79 (3H, d, J=6.6 Hz, (CH$_3$)$_2$CH).

b) 2S-(4-Amino-phenylsulfanylmethyl)-3R-(3-methoxycarbonyl-1S-methylcarbamoyl-propylcarbamoyl)-5-methyl-hexanohydroxamic acid.

2S-(4-Amino-phenylsulfanylmethyl)-3R-(3-methoxycarbonyl-1S-methylcarbamoyl-propylcarbamoyl)- 5-methyl-hexanoic acid (0.50 g, 1.1 mmol) was dissolved in DMF (5 ml) and stirred in an ice bath. HOBT (0.17 g, 1.3 mmole) and WSCDI (0.24 g, 1.3 mmol) were added and the mixture stirred for 30 minutes in the ice bath and 2 hours at room temperature. The mixture was then re-cooled in an ice bath and hydroxylamine hydrochloride (0.11 g, 1.6 mmol) and NMM (0.16 g, 1.6 mmol) added, before stirring at room temperature overnight. DMF was evaporated under high vacuum and the residue dissolved in 1:1 ether/H$_2$O (1:1, 30 ml). The water was separated and evaporated, the resulting residue was purified by column chromatography (acid washed silica gel, 5% methanol/DCM) to give the product as a yellow solid (0.14 g, 0.3 mmole, 27%). m.p. 178.0°–180° C. (decomp.); $^1$H-NMR $\delta_H$; (Methanol-$d_4$), 7.12 (2H, d, J=8.4 Hz, Ar—H), 6.62 (2H, d, J=8.5 Hz, Ar—H), 4.30 (1H, m, CHCH$_2$CH$_2$), 4.79 (3H, s, CO$_2$CH$_3$), 2.91 (1H, m, CHCHCH$_2$S), 2.74 (1H, m, CHCHCH$_2$S), 2.67 (3H, s, CONHCH$_3$), 2.57 (1H, m, CHCHCH$_2$S), 2.33 (3H, m, CHCHCH$_2$S +CH$_2$CH$_2$CO$_2$CH$_3$), 1.81–2.08 (2H, bm, CH$_2$CH$_2$CO$_2$CH$_3$), 1.50 (1H, m, (CH$_3$)2CHCH$_2$), 1.37 (1H, m, (CH$_3$)$_2$CHCH$_2$), 1.02 (1H, m, (CH$_3$)$_2$), 0.84 (3H, d, J=6.3 Hz, (CH$_3$)$_2$CH), and 0.79 (3H, d, J=6.5 Hz, (CH$_3$)$_2$CH); $^{13}$C-NMR $\delta_C$; (Methanol-$d_4$), 175.9,174.8, 173.7, 171.4, 148.0, 134.4, 123.9, 117.2, 65.2, 53.8, 52.3, 48.2, 41.5, 37.7, 31.2, 28.2, 26.9, 26.3, 24.3 and 21.8.

EXAMPLE 6

2S-(Ethylsulfanylmethyl)-3R-(3-methoxycarbonyl-1S-methylcarbamoyl-propylcarbamoyl)- 5-methyl-hexanohydroxamic acid.

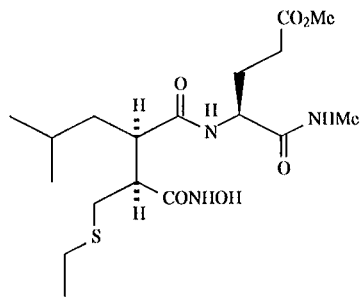

a) 2S-(Ethylsulfanylmethyl)-3R-(3-methoxycarbonyl-1S-methylcarbamoyl-propylcarbamoyl)- 5-methyl-hexanoic acid.

Ethanethiol (5 ml) and triethylamine (0.40 ml, 2.9 mmol) were added to 2-[1R-(3-methoxycarbonyl- 1S-methylcarbamoyl)-3-methylbutyl]-acrylic acid (1.98 g, 5.8 mmol) and the mixture stirred at 35° C., in the dark, under argon overnight. The bulk of the excess thiol was removed in vacuo and cold ether added to the residue. The resulting white solid was filtered and thoroughly washed in cold ether. This was dissolved in EtOAc (20 ml) and washed in 1M hydrochloric acid (2×15 ml), then the ethyl acetate layer was dried over magnesium sulphate and evaporated under vacuum. Recrystallisation of the resultant white solid from EtOAc/hexane provided the product (1.09 g, 2.7 mmol, 47%): $^1$H NMR $\delta_H$; (Methanol-$d_4$), 4.33 (1H, dd, J=5.7, 8.8 Hz, CHCH$_2$CH$_2$), 3.63 (3H, s, CO$_2$CH$_3$), 2.69 (3H, s, CONHCH$_3$), 2.73–2.56 (4H, bm, CHCHCH$_2$S), 2.49 (2H, q, J=7.3 Hz, SCH$_2$CH$_3$), 2.39 (2H, m, CH$_2$CH$_2$CO$_2$CH$_3$), 2.11–1.80 (2H, bm, CH$_2$CH$_2$CO$_2$CH$_3$), 1.63 (1H, m, (CH$_3$)2CHCH$_2$), 1.43 (1H, m, (CH$_3$)$_2$CHCH$_2$), 1.14 (1H, m, (CH$_3$)$_2$CHCH$_2$), 0.86 (3H, d, J=6.5 Hz, (CH$_3$)$_2$CH) and 0.82 (3H, d, J=6.6 Hz, (CH$_3$)$_2$CH).

b) 2S-(Ethylsulfanylmethyl)-3R-(3-methoxycarbonyl-1S-methylcarbamoyl-propylcarbamoyl)- 5-methyl-hexanohydroxamic acid.

2S-(Ethylsulfanylmethyl)-3R-(3-methoxycarbonyl-1S-methylcarbamoyl-propylcarbamoyl)- 5-methyl-hexanoic acid (1.04 g, 2.6 mmol) was taken in DMF (7 ml) and stirred in an ice bath. HOBT (0.42 g, 3.1 mmol) and WSCDI (0.59 g, 3.1 mmol) were added and the mixture stirred for about 30 minutes in an ice bath and a further 2 hours at room temperature. Hydroxylamine hydrochloride (0.26 g, 3.9 mmol) and NMM (0.39 g, 3.9 mmol) were then added at 0° C., and the mixture stirred overnight at room temperature. DMF was evaporated under high vacuum and the resulting residue slurried in ether/water (1:1, 30 ml). The resulting white precipitate was filtered and dried in vacuo. The water layer was separated and evaporated under vacuum and more product isolated from the resulting residue by column chromatography (acid washed silica gel, 5% methanol/DCM). Yield of the combined solids 0.59 g, 1.4 mmol, 55%); m.p 204.5°–206.0° C. (decomp.); $^1$H-NMR $\delta_H$; (Methanol-$d_4$), 4.37 (1H, dd, J=5.7, 8.7 Hz, CHCH$_2$CH$_2$), 3.64 (3H, s, CO$_2$CH$_3$), 2.68 (3H, s, CONHCH$_3$), 2.73–2.28 (8H, bm, CHCHCH$_2$SCH$_2$CH$_3$+CH$_2$CH$_2$CO$_2$CH$_3$), 2.12–1.83 (2H, bm, CHH$_2$CH$_2$CO$_2$CH$_3$), 1.51 (1H, m, (CH$_3$)$_2$CHCH$_2$), 1.39 (1H, m, (CH$_3$)$_2$CHCH$_2$), 1.16 (3H, t, J=7.4 Hz, SCH$_2$CH$_3$), 1.05 (1H, m, (CH$_3$)$_2$CHCH$_2$) 0.85 (3H, d, J=6.4 Hz, (CH$_3$)$_2$CH), and 0.80 (3H, d, J=6.5 Hz, (CH$_3$)$_2$CH); $^{13}$C-NMR $\delta_C$; (Methanol-$d_4$), 175.7, 174.3, 173.4, 171.2, 53.4, 51.9, 48.2, 47.8, 41.3, 32.3, 30.8, 27.8, 26.5, 26.5, 25.9, 24.0, 21.4 and 14.6.

EXAMPLE 7

2S-(Acetylsulfanylmethyl)-3R-(3-methoxycarbonyl-1S-methylcarbamoyl-propylcarbamoyl)- 5-methyl-hexanohydroxamic acid.

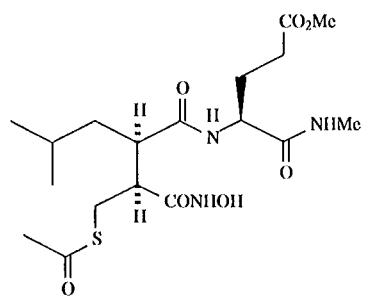

a) 2S-(Acetylsulfanylmethyl)-3R-(3-methoxycarbonyl-1S-methylcarbamoyl-propylcarbamoyl)- 5-methyl-hexanoic acid.

To 2-[1R-(3-methoxycarbonyl-1S-methylcarbamoyl)-3-methylbutyl]-acrylic acid (1.53 g, 4.5 mmol) was added thiolacetic acid (4 ml) and the mixture stirred at room temperature, overnight, in the dark, under argon. Diethyl ether (30 ml) was added to the mixture and the resulting white precipitate filtered and thoroughly washed in cold ether to give the product (1.54 g, 3.7 mmol, 82%); $^1$H NMR $\delta_H$; (Methanol-$d_4$), 4.34 (1H, dd, J=5.7, 8.5 Hz, CHCH$_2$CH$_2$), 3.62 (3H, s, CO$_2$CH$_3$), 3.14 (1H, dd, J=3.4, 13.7 Hz, CHCHCH$_2$S), 2.91 (1H, m, CHCHCH$_2$S), 2.69 (3H, s, CONHCH$_3$), 2.67 (2H, m, CHCHCH$_2$S), 2.30 (2H, m, CH$_2$CH$_2$CO$_2$CH$_3$), 2.27 (3H, s, SCOCH$_3$), 2.11–1.81 (2H, bm, CH$_2$CH$_2$CO$_2$CH$_3$), 1.67 (1H, m, (CH$_3$)$_2$CHCH$_2$), 1.44 (1H, m, (CH$_3$)$_2$CHCH$_2$), 1.02 (1H, m, (CH$_3$)$_2$CHCH$_2$), 0.87 (3H, d, J=6.5 Hz, (CH$_3$)$_2$CH), and 0.83 (3H, d, J=6.5 Hz, (CH$_3$)$_2$CH).

b) 2S-(Acetylsulfanylmethyl)-3R-(3-methoxycarbonyl-1S-methylcarbamoyl-propylcarbamoyl)- 5-methyl-hexanohydroxamic acid.

2S-(Acetylsulfanylmethyl)-3R-(3-methoxycarbonyl-1S-methylcarbamoyl-propylcarbamoyl)- 5-methyl-hexanoic acid (1.49 g, 3.6 mmol) was dissolved in DMF (10 ml) and stirred in an ice bath. HOBT (0.58 g, 4.3 mmol) and WSCDI (0.82 g, 4.3 mmol were added and the mixture stirred for about 30 minutes in the ice bath and a further 2 hours at room temperature. Hydroxylamine hydrochloride (0.37 g, 5.4 mmol) and NMM (0.54 g, 5.4 mmol) were then added at 0° C., and the mixture stirred overnight at room temperature. DMF was evaporated under high vacuum and the resulting residue slurried in ether/H$_2$O (1:1, 50 ml). The resulting white precipitate was filtered and dried in vacuo. A second batch of product was isolated from the aqueous layer following column chromatography (acid washed silica gel, 5% methanol/DCM) to give (0.59 g, 1.4 mmol, 38%); m.p. 179.0° C.–180.0° C.; $^1$H NMR $\delta_H$;(Methanol-$d_4$), 4.38 (1H, dd, J=5.8, 8.6 Hz, CHCH$_2$CH$_2$), 3.61 (3H, s, CO$_2$CH$_3$), 3.04 (1H, dd, J=4.0, 13.2 Hz, CHCHCH$_2$S), 2.89 (1H, dd, J=10.7, 13.2 Hz, CHCHCH$_2$S), 2.69 (3H, s, CONHCH$_3$), 2.51 (1H, m, CHCHCH$_2$S), 2.40 (2H, m, CH$_2$CH$_2$CO$_2$CH$_3$), 2.35 (1H, m, CHCHCH$_2$S), 2.25 (3H, s, SCOCH$_3$), 2.13–1.83 (2H, bm, CH$_2$CH$_2$CO$_2$CH$_3$), 1.53 (1H, m, (CH$_3$)$_2$CHCH$_2$), 1.42 (1H, m, (CH$_3$)$_2$CHHCH$_2$), 1.03 (1H, m, (CH$_3$)$_2$CHCH$_2$), 0.85 (3H, d, J=6.4 Hz, (C$\underline{H}_3$)$_2$CH), and 0.81 (3H, d, J=6.6 Hz, (C$\underline{H}_3$)$_2$CH); $^{13}$C-NMR $\delta_C$; (Methanol-d$_4$), 196.4, 176.0, 175.2, 174.2, 171.4, 54.3, 52.3, 48.4, 48.1, 41.7, 31.5, 30.8, 30.6, 28.5, 27.2, 26.6, 24.6 and 22.1.

EXAMPLE 8

2S-(Benzylsulfanylmethyl)-3R-(3-methoxycarbonyl-1S-methylcarbamoyl-propylcarbamoyl)- 5-methyl-hexanohydroxamic acid.

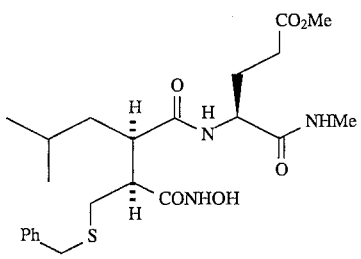

a) 2S-(Benzylsulfanylmethyl)-3R-(3-methoxycarbonyl-1S-methylcarbamoyl-propylcarbamoyl)- 5-methyl-hexanoic acid.

Benzyl mercaptan (4 ml), methanol (1 ml) and triethylamine (0.21 ml, 1.5 mmol) were added to 2-[1R-(3-methoxycarbonyl-1S-methylcarbamoyl)-3-methylbutyl]-acrylic acid (1.05 g, 3.1 mmol) and the mixture stirred overnight in the dark under argon at 60° C. The crude mixture was purified by column chromatography (silica gel, 2–10% methanol/DCM) to give the desired product (0.35 g, 0.7 mmol, 24%); $^1$H NMR $\delta_H$; (Methanol-d$_4$), 7.21 (5H, m, Ph—H), 4.30 (1H, dd, J=6.0, 8.5 Hz, C$\underline{H}$CH$_2$CH$_2$), 3.65 (2H, m, C$\underline{H}_2$Ph), 3.59 (3H, s, CO$_2$C$\underline{H}_3$), 2.67 (3H, s, CONHC$\underline{H}_3$), 2.81–2.18 (6H, bm, C$\underline{H}$C$\underline{H}_2$S+CH$_2$C$\underline{H}_2$CO$_2$CH$_3$), 2.04–1.73 (2H, bm, C$\underline{H}_2$CH$_2$CO$_2$CH$_3$), 1.65 (1H, m, (CH$_3$)$_2$CHC$\underline{H}_2$), 1.41 (1H, m, (CH$_3$)$_2$C$\underline{H}$CH$_2$), 1.08 (1H, m, (CH$_3$)$_2$CHC$\underline{H}_2$), 0.83 (3H, d, J=6.5 Hz, (C$\underline{H}_3$)$_2$CH) and 0.80 (3H, d, J=6.6 Hz, (C$\underline{H}_3$)$_2$CH).

b) 2S-(Benzylsulfanylmethyl)-3R-(3-methoxycarbonyl-1S-methylcarbamoyl-propylcarbamoyl)- 5-methyl-hexanohydroxamic acid.

2S-(Benzylsulfanylmethyl)-3R-(3-methoxycarbonyl-1S-methylcarbamoyl-propylcarbamoyl)- 5-methyl-hexanoic acid (0.35 g, 0.7 mmol) was dissolved in DMF (5 ml) and stirred in an ice bath. HOBT (0.12 g, 0.9 mmol) and WSCDI (0.17 g, 0.9 mmol) were added and the mixture stirred for a further about 30 minutes in the ice bath, followed by 2 hours at room temperature. Hydroxylamine hydrochloride (0.08 g, 1.1 mmol) and NMM (0.11 g, 1.1 mmol) were added whilst stirring in an ice bath, then the mixture allowed to warm to room temperature overnight. DMF was evaporated under high vacuum and the crude residue slurried in ether/H$_2$O (1:1, 30 ml). The resulting white precipitate was filtered and thoroughly washed in water and ether, before drying in vacuo (0.17 g, 0.4 mmol, 47%); m.p. 187°–188° C. (decomposition); $^1$H-NMR $\delta_H$;(methanol-d$_4$), 7.20 (5H, m, Ph—H), 4.25 (1H, dd, J=6.0, 8.4 Hz, C$\underline{H}$CHCH$_2$), 3.61 (5H, m, CO$_2$C$\underline{H}_3$ +C$\underline{H}_2$Ph), 2.67 (3H, s, CONHC$\underline{H}_3$), 2.62–2.35 (3H, bm, CHC$\underline{H}_2$S), 2.33–2.05 (3H, bm, C$\underline{H}$CH$_2$S+CH$_2$CH$\underline{H}_2$CO$_2$CH$_3$), 1.99–1.66 (2H, bm, C$\underline{H}_2$CH$_2$CO$_2$CH$_3$), 1.54 (1H, m, (CH$_3$)$_2$C$\underline{H}$CH$_2$), 1.39 (1H, m, (CH$_3$)$_2$CHC$\underline{H}_2$), 0.84 (3H, d, J=6.4 Hz, (C$\underline{H}_3$)$_2$CH) and 0.80 (3H, d, J=6.5 Hz, (C$\underline{H}_3$)$_2$CH); $^{13}$C NMR $\delta_C$; (Methanol-d$_4$), 176.2, 175.0, 174.0, 171.9, 140.0, 130.5, 129.8, 128.7, 54.2, 52.6, 42.0, 37.0, 32.4, 31.6, 28.4, 27.2, 26.6, 24.7 and 22.1.

EXAMPLE 9

2S-(tert-Butylsulfanylmethyl)-3R-(3-methoxycarbonyl-1S-methylcarbamoyl-propylcarbamoyl)- 5-methyl-hexanohydroxamic acid.

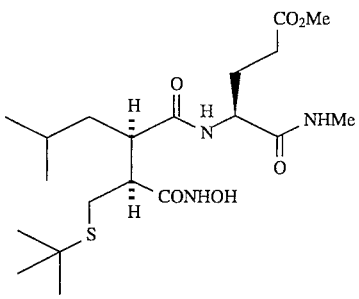

a) 2S-( tert-Butylsulfanylmethyl)-3R-(3-methoxycarbonyl-1S-methylcarbamoyl-propylcarbamoyl)- 5-methyl-hexanoic acid.

2-[1R-(3-Methoxycarbonyl-1S-methylcarbamoyl)-3-methylbutyl]-acrylic acid (1.28 g, 3.7 mmol) was taken up in methanol (5 ml) and treated with tert-butyl mercaptan (5 mL) and triethylamine (0.26 mL, 1.9 mmol) and stirred at 50° C., in the dark, under argon for 72 hours. The bulk of the excess thiol was removed in-vacuo and the residue purified by column chromatography (silica gel, 0 to 10% methanol in DCM) provided the product as a white foam (0.26 g, 0.6 mmol, 16%): $^1$H NMR $\delta_H$; (Methanol-d$_4$), 4.55 (1H, m, C$\underline{H}$CH$_2$CH$_2$), 3.70 (3H, s, CO$_2$C$\underline{H}_3$), 2.98–2.67 (6H, bm, CHC$\underline{H}$CH$_2$S and CONHC$\underline{H}_3$), 2.58 (1H, m, C$\underline{H}$CHCH$_2$S), 2.45 (2H, m, CH$_2$C$\underline{H}_2$CO$_2$CH$_3$), 2.20–1.86 (2H, bm, C$\underline{H}_2$CH$_2$CO$_2$CH$_3$), 1.70 (1H, m, (CH$_3$)$_2$CHC$\underline{H}_2$), 1.42 (1H, m, (CH$_3$)$_2$C$\underline{H}$CH$_2$), 1.25 (9H, s, SC(C$\underline{H}_3$)$_3$), 1.18 (1H, m, (CH$_3$)$_2$CHC$\underline{H}_2$), and 1.00–0.78 (6H, bm, (C$\underline{H}_3$)$_2$CH).

b) 2S-( tert-Butylsulfanylmethyl)-3R-(3-methoxycarbonyl-1S-methylcarbamoyl-propylcarbamoyl)- 5-methyl-hexanohydroxamic acid.

2S-( tert-Butylsulfanylmethyl)-3R-(3-methoxycarbonyl-1S-methylcarbamoyl-propylcarbamoyl)- 5-methyl-hexanoic acid (0.24 g, 0.6 mmol) was taken in DMF (3 ml) and stirred in an ice bath. HOBT (0.09 g, 0.7 mmol) and WSCDI (0.12 g, 0.7 mmol) were added and the mixture stirred for about 30 minutes in an ice bath and a further 2 hours at room temperature. Hydroxylamine hydrochloride (0.06 g, 0.8 mmol) and NMM (0.39 g, 3.9 mmol) were then added at 0° C., and the mixture stirred overnight at room temperature. DMF was evaporated under high vacuum and the resulting residue slurried in ether/water (1:1, 30 ml). The resulting white precipitate was filtered and dried in vacuo (0.07 g, 0.2 mmol, 29%): m.p 195.0°–196.0° C. (decomp.); $^1$H NMR $\delta_H$; (Methanol-d$_4$), 4.37 (1H, dd, J=5.7, 8.6 Hz, C$\underline{H}$CH$_2$CH$_2$), 3.62 (3H, s, CO$_2$C$\underline{H}_3$), 2.69 (3H, s, CONHC$\underline{H}_3$), 2.48–2.22 (5H, bm, C$\underline{H}$CHC$\underline{H}_2$SC$\underline{H}_2$CH$_3$ +C$\underline{H}_2$CH$_2$CO$_2$CH$_3$), 1.97 (2H, bm, C$\underline{H}_2$CH$_2$CO$_2$CH$_3$), 1.52 (1H, m, (CH$_3$)$_2$CHC$\underline{H}_2$), 1.40 (1H, m, (CH$_3$)$_2$C$\underline{H}_{CH2}$), 1.23 (9H, s, SC(C$\underline{H}_3$)$_3$), 1.04 (1H, m, (CH$_3$)$_2$CHC$\underline{H}_2$) 0.85 (3H, d, J=6.4 Hz, (C$\underline{H}_3$)$_2$CH), and 0.80 (3H, d, J=6.5 Hz, (C$\underline{H}_3$)$_2$CH); $^{13}$C NMR $\delta_C$; (Methanol-d$_4$), 176.5, 174.9, 174.0, 171.9, 54.2, 52.5, 49.2, 48.8, 48.3, 43.6, 41.9, 31.6, 30.1, 28.7, 27.2, 26.6, 24.7, and 22.1.

EXAMPLE 10

2S-Thiomethyl-3R-(3-methoxycarbonyl-1S-methylcarbamoyl-propylcarbamoyl)-5-methyl-hexanohydroxamic acid.

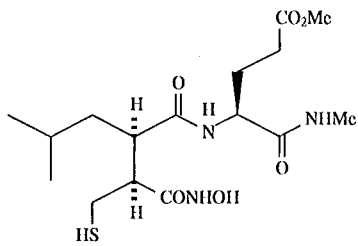

2S-(Acetylsulfanylmethyl)-3R-(3-methoxycarbonyl-1S-methylcarbamoyl-propylcarbamoyl)- 5-methyl-hexanohydroxamic acid (0.12 g, 0.3 mmol) was dissolved in dry methanol (10 mL) and to this solution was added sodium methoxide in methanol (prepared by dissolving sodium metal (0.01 g, 0.6 mmol) in dry methanol (5 mL)). The resultant solution was stirred at room temperature for 3 hours then ion exchange resin added to neutralise excess base. The resin was removed by filtration and washed with methanol then the combined filtrates evaporated under vacuum to give the product as a white solid (0.01 g, 0.3 mmol, 95%); m.p. 183.5°–185.5° C.; $^1$H NMR $\delta_H$; (Methanol-$d_4$), 4.33 (1H, m, C$\underline{H}$CH$_2$CH$_2$), 3.52 (3H, s, CO$_2$C$\underline{H}_3$), 2.75–2.49 (6H, bm, CHCHCH$_2$S and CONHC$\underline{H}_3$), 2.45–2.20 (3H, bm, C$\underline{H}$CHCH$_2$S and CH$_2$CH$_2$CO$_2$CH$_3$), 2.12–1.78 (2H, bm, CH$_2$CH$_2$CO$_2$CH$_3$), 1.71–1.33 (2H, bm, (CH$_3$)$_2$CHC$\underline{H}_2$), 1.07 (1H, m, (CH$_3$)$_2$C$\underline{H}$CH$_2$), and 0.95–0.72 (6H, bm, (C$\underline{H}_3$)$_2$CH); $^{13}$C-NMR $\delta_C$; (Methanol-$d_4$), 175.9, 174.5, 173.3, 171.3, 53.5, 52.0, 41.8, 32.9, 31.1, 27.9, 26.7, 26.1, 24.4, and 21.7.

EXAMPLE 11

2S-(4-Hydroxyphenylsulfanylmethyl)-3R-(2-tert-butoxycarbonyl-1S-methylcarbamoyl-ethylcarbamoyl)- 5-methyl-hexanohydroxamic acid.

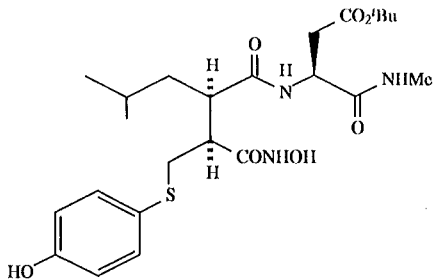

a) N-methyl-2S-(N-Benzyloxycarbonylamino)-3-tert-butoxycarbonyl propionamide.

2S-(N-Benzyloxycarbonylamino)-3-tert-butoxycarbonyl propionic acid (9.96, 29.2 mmol) was taken up in DCM (80 ml). The solution was cooled to 0° C., while pentafluorophenol (6.44 g, 35.0 mmol) and WSCDI (6.71 g, 35.0 mmol) were added. The reaction was stirred for 0° C for about 30 minutes then room temperature for 2 hours. Mixture was then cooled to 0° C and methylamine in abs. ethanol (7.3 ml, 58.4 mmol) added dropwise. The mixture was allowed to warm to room temperature and stirred overnight. Further DCM (70 ml) was added, and the mixture washed with 1M sodium carbonate (2×70 ml), 1M hydrochloric acid (2×70 ml) and brine (1×70 ml). The organic layer was dried over magnesium sulphate and the solvent removed under reduced pressure to give the product as a white solid (9.8 g, 29.2 mmol, 100%): $^1$H-NMR; $\delta_H$ (CDCl$_3$), 7.36 (5H, s, Ph—H), 6.52 (1H, bm, N$\underline{H}$CH$_3$), 5.12 (2H, s, C$\underline{H}_2$Ph), 4.50 (1H, m, C$\underline{H}$CH$_2$CO$_2$), 2.91 (1H, dd, J=4.6, 16.9 Hz, CHC$\underline{H}_2$CO$_2$), 2.79 (3H, d, J=4.9 Hz, NHC$\underline{H}_3$), 2.63 (1H, dd, J=6.5 17.0 Hz, CHC$\underline{H}_2$CO$_2$), and 1.43 (9H, s, CO$_2$C(C$\underline{H}_3$)$_3$).

b) N-methyl-2S-amino-3-tert-butoxycarbonyl propionamide.

N-Methyl-2S-(N-benzyloxycarbonylamino)-3-tert-butoxycarbonyl propionamide (5.21 g, 15.4 mmol) was taken up in methanol (100 ml), and the resultant solution purged with argon. 10% Pd/C catalyst (1 g) was added as a slurry in EtOAc, and hydrogen gas bubbled through the mixture for about 30 minutes. The catalyst was filtered off and the filterate evaporated under reduced pressure to give the product as a white solid (3.13 g, 15.4 mmol, 100%); $^1$H-NMR $\delta_H$; (DMSO-$d_6$), 7.80 (1H, m, N$\underline{H}$CH$_3$), 3.43 (1H, m, C$\underline{H}$CH$_2$CO$_2$), 2.59(1H, d, J=4.6 Hz, NHC$\underline{H}_3$), 2.54 (1H, m, C$\underline{H}$CH$_2$CO$_2$), 2.30 (1H, dd, J=7.7, 15.5 Hz, CHC$\underline{H}_2$CO$_2$), 1.86 (1H, bs, H$_2$NC$\underline{H}$), and 1.39 (9H, s, CO$_2$C(C$\underline{H}_3$)$_3$).

c) 2-[1R-(2-tert-Butoxycarbonyl-1S-methylcarbamoyl-ethylcarbamoyl)-3methylbutyl]-malonic acid dibenzylester. N-methyl-2S-amino-3-tert-butoxycarbonyl propionamide (3.10 g, 15.3 mmol) was taken up in DMF (80 ml) and 2-benzyloxycarbonyl-3R-isobutyl succinic acid 4-pentafluorophenyl- 1-benzyl diester (7.87 g, 13.9 mmol) added and the mixture was stirred at 20° C. for 72 hours. Solvent was removed under reduced pressure, the residue taken up in DCM (200 ml) and washed in 1M sodium carbonate (2×150 ml), 1M hydrochloric acid (1×150 ml) and brine (1×150 ml). The organic layer was dried over magnesium sulphate and evaporated under reduced pressure to a yellow oil, which was purified by column chromatography (silica gel, 0–5% methanol/DCM) to give a white, foamy solid (6.64 g, 12.0 mmol, 86%); $^1$H NMR $\delta_H$; (CDCl$_3$), 7.32 (10H, bm, Ph—H), 7.06 (1H, m, CONHCH), 5.30–5.00 (4H, bm, 2×C$\underline{H}_2$Ph), 4.60 (1H, m, C$\underline{H}$CH$_2$CO$_2^t$Bu), 3.83 (1H, d, J=9.2 Hz, C$\underline{H}$CH(CO$_2$Bzl)$_2$), 2.97 (1H, m, CHC$\underline{H}$(CO$_2$Bzl)$_2$), 2.78 (1H, m, CHC$\underline{H}_2$CO$_2^t$Bu), 2.50 (1H, dd, J=6.6, 17.2 Hz, CHC$\underline{H}_2$CO$_2^t$Bu), 1.68 (1H, m, (CH$_3$)$_2$CHC$\underline{H}_2$), 1.60 (1H, m, (CH$_3$)$_2$C$\underline{H}$CH$_2$), 1.46 (9H, s, CO$_2$C(C$\underline{H}_3$)$_3$), 1.10 (1H, m, (CH$_3$)$_2$CHC$\underline{H}_2$), and 0.83 (6H, m, (C$\underline{H}_3$)$_2$CH).

d) 2-[1R-(2-tert-Butoxycarbonyl-1S-methylcarbamoyl-ethylcarbamoyl)-3-methylbutyl]-acrylic acid.

2-[1R-(2-tert-Butoxycarbonyl-1S-methylcarbamoyl-ethylcarbamoyl)-3-methylbutyl]-malonic acid dibenzylester (6.60 g, 11.9 mmol) was taken up in EtOH (100 ml) and the resultant solution purged with argon. 10% Pd/C catalyst (2 g) was added as a slurry in EtOAc. Hydrogen was bubbled through the mixture for about 30 minutes, before removal of the catalyst by filtration. The filtrate was cooled to 0° C. and piperidine (1.07 g, 12.6 mmol) added followed by aqueous formaldehyde (8.6 ml, 115 mmol). This mixture was stirred overnight, warming to room temperature. Solvent was removed under reduced pressure and the residue taken up in EtOAc (100 ml). This was washed in 1M hydrochloric acid (1×50 ml) and extracted with 1M sodium carbonate (2×70 ml). The aqueous extracts were combined and acidified to pH3 by dropwise addition of 2M hydrochloric acid. The product was extracted from the acidified aqueous layer with EtOAc (2×100 ml). This was dried over magnesium sulphate and evaporated under reduced pressure to a white solid (2.75 g, 7.5 mmol, 65%); $^1$H NMR $\delta_H$; (CDCl$_3$), 7.95 (1H, d, J=8.6 Hz, CONHCH), 6.98 (1H, m, CONHCH$_3$), 6.46 (1H, s, C=CH$_2$), 5.91 (1H, s, C=CH$_2$), 4.84 (1H, m, CHCH$_2$CO$_2^t$Bu), 3.71 (1H, m, CH$_2$CHCCH$_2$), 2.81 (3H, d, J=4.8 Hz, CONHCH$_3$), 2.64 (2H, m, CHCH$_2$CO$_2^t$Bu), 1.79 (1H, m, (CH$_3$)$_2$CHCH$_2$), 1.56–1.42 (2H, bm, (CH$_3$)$_2$CHCH$_2$), 1.40 (9H, s, CO$_2$C(CH$_3$)$_3$), and 0.88 (6H, m, (CH$_3$)$_2$CH).

e) 2S-(4-Hydroxyphenylsulfanylmethyl)-3R-(2-tert butoxycarbonyl-1S-methylcarbamoyl-ethylcarbamoyl)- 5-methyl-hexanoic acid.

2-[1R-(2-tert-Butoxycarbonyl-1S-methylcarbamoyl-ethylcarbamoyl)-3-methylbutyl]-acrylic acid (2.70 g, 7.3 mmol) was taken up in methanol (5 ml), 4-hydroxythiophenol (2.50 g, 20.0 mmol) added and the mixture was then stirred at 60° C., under argon, in the dark for 72 hours. Solvent removal gave a yellow oil which was purified by column chromatography (silica gel, 2–10% methanol/DCM) to give the title compound as a white solid (2.92 g, 5.9 mmol, 80%). $^1$H NMR $\delta_H$; (methanol-d$_4$), 7.24 (2H, d, J=8.6 Hz, Ar—H), 6.68 (2H, d, J=8.5 Hz, Ar—H), 4.62 (1H, m, CHCH$_2$CO$_2^t$Bu), 2.82 (1H, m, CHCHCH$_2$S), 2.76–2.49 (6H, bm, CHCHCH$_2$S and CHCH$_2$CO$_2^t$Bu), 2.66 (3H, s, CONHCH$_3$), 1.60 (1H, m, (CH$_3$)$_2$CHCH$_2$), (9H, s, CO$_2$C(CHH$_3$)$_3$), 1.18 (1H, m, (CH$_3$)$_2$CHCH$_2$), 1.01 (1H, m, (CH$_3$)$_2$CHCH$_2$), 0.82 (3H, d, J=6.6 Hz, (CH$_3$)$_2$CH), and 0.79 (3H, d, J=6.7 Hz, (CH$_3$)$_2$CH).

f) 2S-(4-Hydroxyphenylsulfanylmethyl)-3R-(2-tert butoxycarbonyl-1S-methylcarbamoyl-ethylcarbamoyl)- 5-methyl-hexanohydroxamic acid.

2S-(4-Hydroxyphenylsulfanylmethyl)-3R-(2-tert butoxycarbonyl-1S-methylcarbamoyl-ethylcarbamoyl)- 5-methyl-hexanoic acid (2.21 g, 4.4 mmol) was taken up in 10% DMF in DCM (40 ml) and the solution cooled to 0° C., while pentafluorophenol (0.98 g, 5.3 mmol) and WSCDI (1.02 g, 5.3 mmol) added. The reaction mixture was stirred for 2 hours at room temperature. Solvent was removed under reduced pressure and the residue taken up in DCM and washed in 1M sodium carbonate (2×50 ml), 1M hydrochloric acid (1×50 ml) and brine. (1×50 ml). The organic layer was dried over magnesium sulphate and the solvent removed under reduced pressure to give a foamy solid (1.5 g, 2.3 mmol, 52%). This solid was taken up in DMF (20 ml) and hydroxylamine hydrochloride (0.48 g, 7 mmol) added, followed by NMM (0.52 g, 5.1 mmol) and the mixture was stirred for 1 hour. DMF was evaporated under reduced pressure (high vacuum), the resulting residue was taken up in DCM (50 ml) and the product extracted with water (4×50 ml). Aqueous extractions were combined and evaporated under reduced pressure, the resulting residue was purified by column chromatography (acid washed silica gel, 5% methanol/DCM), to give the product as a white power (0.28 g, 0.6 mmol, 24%); m.p. 153.0° C.; Analysis for C$_{24}$H$_{37}$N$_3$O$_7$S; requires C 56.34 H 7.29 N 8.21: Found C 55.31 H 7.24 N 7.96; $^1$H NMR $\delta_H$; (methanol-d$_4$), 7.21 (2H, d, J=8.6 Hz, Ar—H), 6.68 (2H, d, J=8.7 Hz, Ar—H), 4.61 (1H, dd, J=5.5, 8.7 Hz, CHCH$_2$CO$_2^t$Bu), 2.91 (1H, dd, J=3.6, 13.1 Hz , CHCHCHhd 2S), 2.79 (1H, m, CHCHCH$_2$S), 2.70–2.55 (2H, bm, CHCH$_2$CO$_2^t$Bu), 2.67 (3H, s, CONHCH$_3$), 2.51 (1H, m, CHCHCH$_2$S), 2.32 (1H, dt, J=3.6, 10.9 Hz, CH$_2$CHCH), 1.50 (1H, m, (CH$_3$)$_2$CHCH$_2$), 1.43–1.25 (1H, m, (CH$_3$)$_2$CHCH$_2$), 1.40 (9H, s, CO$_2$(CH$_3$)$_3$), 1.00 (1H, m, (CH$_3$)$_2$CHCH$_2$), 0.83 (3H, d, J=6.6 Hz, (CH$_3$)$_2$CH), and 0.79 (3H, d, J=6.6 Hz, (CH$_3$)$_2$CH); $^{13}$C NMR $\delta_C$; (methanol-d$_4$), 175.7, 173.0, 171.4, 171.2, 158.1, 134.3, 125.8, 117.1 82.4, 51.4, 48.2, 48.1, 41.4, 37.9, 36.9, 28.4, 26.9, 26.3, 24.2 and 21.8.

EXAMPLE 12

2S-(4-Hydroxyphenylsulfanylmethyl)-3R-(3-tert butoxycarbonyl-1S-methylcarbamoyl-propylcarbamoyl)- 5-methyl-hexanohydroxamic acid.

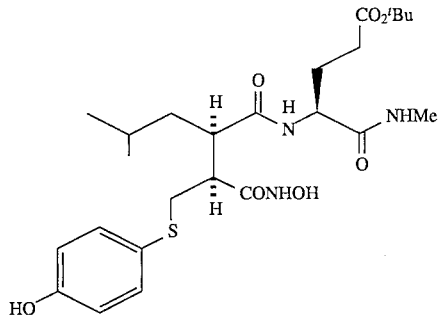

a) N-methyl-2S-(N-Benzyloxycarbonylamino)-4-tert-butoxycarbonyl butanamide.

2S-(N-Benzyloxycarbonylamino)-4-tert-butoxycarbonyl butanoic acid (7.43, 22.0 mmol) was taken up in DCM (70 ml) and the solution cooled to 0° C., while pentafluorophenol (4.9 g, 26.5 mmol) and WSCDI (5.05 g, 26.5 mmol) were added. The reaction was stirred at 0° C. for about 30 minutes then at room temperature for 2 hours. The mixture was then cooled to 0° C. and methylamine in absolute ethanol (5.5 ml, 44.1 mmol) added dropwise. The mixture was warmed to room temperature overnight, DCM (60 ml) was added, and the mixture washed with 1M sodium carbonate (2×70 ml), 1M hydrochloric acid (2×70 ml) and brine (1×70 ml). The organic layer was dried over magnesium sulphate and the solvent removed under reduced pressure to give the product as a white solid (7.74 g, 22.1 mmol, 100%): $^1$H NMR $\delta_H$; (CDCl$_3$), 7.32 (5H, s Ar—H), 6.52 (1H, bm, CONHMe), 5.85 (1H, d, J=7.9 Hz, ZNHCH), 5.17–5.02 (2H, bm, PhCH$_2$O), 4.19 (1H, m, HNCHCONHMe), 2.77 (3H, d, J=4.7 Hz, CONHCH$_3$), 2.32 (2H, m, CH$_2$CH$_2$CO$_2^t$Bu), 1.99 (2H, m, CH$_2$CH$_2$CO$_2^t$BU), and 1.43 (9H, s, CO$_2$C(CH$_3$)$_3$).

b) N-methyl-2S-amino-4-tert-butoxycarbonyl butanamide. N-methyl-2S-(N-Benzyloxycarbonylamino)-4-tert-butoxycarbonyl butanamide (7.70 g, 21.9 mmol) was taken up in methanol (150 ml) and the resultant solution purged with argon. 10% Pd/C catalyst (1 :1 g) was added as a slurry in EtOAc and hydrogen gas bubbled through the mixture for about 30 minutes. The catalyst was filtered off and the filtrate evaporated under reduced pressure to the product as a white solid (4.75 g, 21.9 mmol, 100%): $^1$H NMR $\delta_H$; (DMSO-d$_6$), 7.77 (1H, m, CONHCH$_3$), 3.08 (1H, dd, J=5.2, 7.9 Hz, H$_2$NCHCO), 2.58 (3H, d, J=4.6 Hz, CONHCH$_3$), 2.22 (2H, m, CH$_2$CHH$_2$CO$_2^t$Bu), 1.89–0.97 (2H, bm, CH$_2$CH$_2$CO$_2^t$BU) and 1.39 (9H, s, CO$_2$C(CH$_3$)$_3$).

c) 2-[1R-(3-tert-Butoxycarbonyl-1S-methylcarbamoylopropylcarbamoyl)-3-methylbutyl]-malonic acid dibenzylester.

N-methyl 2S-amino-4-tert-butoxycarbonyl butanamide (4.70 g, 21.7 mmol) was taken up in DMF (80 ml), 2-benzyloxycarbonyl-3R-isobutyl succinic acid 4-pentafluorophenyl- 1-benzyl diester (11.15 g, 19.8 mmol) added and the mixture was stirred at 22° C. for 72 hours. Solvent was removed under reduced pressure and the residue taken up in DCM (200 ml) and washed in 1M sodium carbonate (2×150 ml), 1M hydrochloric acid (1×150 ml) and brine (1×150 ml). The organic layer was dried over magnesium sulphate and evaporated under vacuum to a yellow oil, which was purified by column chromatography (silica gel, 1:1 EtOAc/Hexane) to give a white solid, which was recrystallised from EtOAc/ hexane (6.8 g, 12.0 mmol, 60.9%); $^1$H NMR $\delta_H$; (CDCl$_3$), 7.27 (10H, bm, Ar—H), 6.91 (1H, m, CONHCH), 6.48 (1H, m, CONHCH$_3$), 5.13 (4H, bm, 2×CH$_2$Ph), 4.33 (1H, m, C HCH$_2$CH$_2$), 3.82 (1H, d, J=9.7 Hz, CHCH(CO$_2$Bzl)$_2$), 2.96 (1H, dt, J=3.9, 10.0 Hz, CHCH(CO$_2$Bzl)$_2$), 2.78 (3H, d, J=4.8 Hz, CONHCH$_3$), 2.51–2.22 (2H, m, CH$_2$C H$_2$CO$_2$$^t$Bu), 2.12–1.83 (2H, m, CH$_2$CH$_2$CO$_2$$^t$Bu), 1.61 (1H, m, (CH$_3$)$_2$CHCH$_2$), 1.46 (1H, m, (CH$_3$)$_2$CHCH$_2$), 1.44 (9H, s, CO$_2$C(CH$_3$)$_3$), 1.10 (1H, m, (CH$_3$)$_2$CHCH$_2$) and 0.83 (6H, m, (CH$_3$)$_2$CH).

d) 2-[1R-(3-tert-Butoxycarbonyl-1S-methylcarbamoyl-propylcarbamoyl)-3-methylbutyl]-acrylic acid.

2-[1R-(3-tert-Butoxycarbonyl-1S-methylcarbamoyl-propylcarbamoyl)-3-methylbutyl]-malonic acid dibenzylester (6.65 g, 11.8 mmol) was taken up in EtOH (100 ml) and the resultant solution purged with argon. 10% Pd/C catalyst (1.5 g) was added as a slurry in EtOAc. Hydrogen gas was bubbled through the mixture for about 30 minutes, before removal of the catalyst by filtration. To the filtrate was added piperidine (1.09 g, 12.8 mmol) at 0° C. followed by aqueous formaldehyde (8.7 ml, 116 mmol) dropwise. The mixture was stirred overnight, at room temperature. Solvent was removed under reduced pressure and the residue taken up in EtOAc (100 ml). This was washed in 1M hydrochloric acid (1×50 ml) and extracted with 1M sodium carbonate (2×70 ml). The extractions were combined and acidified to pH3 by the dropwise addition of 2M hydrochloric acid. The product was extracted from the aqueous by EtOAc (2×100 ml), the combined organic phases were dried over magnesium sulphate and evaporated under reduced pressure to a white solid (3.36, 8.7 mmol, 75%); $^1$H NMR $\delta_H$; (CDCl$_3$), 7.96 (1H, d, J=8.6 Hz, CONHCH), 7.01 (1H, m, CONHCH$_3$), 6.45 (1H, s, C=CH$_2$), 5.94 (1H, s, C=CH$_2$), 4.61 (1H, m, COC HNH), 3.78 (1H, m, CH$_2$CHCCCH$_2$), 2.84 (3H, d, J=4.8 Hz, CONHCH$_3$), 2.24 (2H, m, CH$_2$CH$_2$CO$_2$$^t$Bu), 2.09–1.77 (2H, bm, CH$_2$CH$_2$CO$_2$$^t$Bu), 1.79 (1H, m, (CH$_3$)$_2$CHCH$_2$), 1.58–1.35 (2H, bm, (CH$_3$)$_2$CHCH$_2$), 1.42 (9H, s, CO$_2$C(C H$_3$)$_3$), a 0.88 (6H, m, (CH$_3$)$_2$CH).

e) 2S-(4-Hydroxyphenylsulfanylmethyl)-3R-(2-tert butoxycarbonyl-1S-methylcarbamoyl-propylcarbamoyl)- 5-methyl-hexanoic acid.

2-[1R-(3-tert-Butoxycarbonyl-1S-methylcarbamoyl-propylcarbamoyl)-3-methylbutyl]-acrylic acid (3.34 g, 8.68 mmol) was taken up in methanol (7 ml) and 4-hydroxythiophenol (2.74 g, 21.7 mmol) added, the mixture was then stirred at 60° C. under argon, in the dark for 60 hours. Solvent was removed by evaporation under vacuum and the resulting crude oil purified by column chromatography (silica gel, 0–10% methanol/DCM). The resulting product was further purified by column chromatography (silica gel, 60–100% EtOAc/hexane) to give the title compound as a white solid (2.22 g, 4.3 mmol, 50%); $^1$H NMR $\delta_H$; (methanol-d$_4$), 7.23 (2H, d, J=8.6 Hz, Ar—H), 6.69 (2H, d, J=8.7 Hz, Ar—H), 4.25 (1H, dd, J=5.7, 8.7 Hz, C HCH$_2$CH$_2$CO$_2$$^t$Bu), 2.85 (2H, m, CHCHCH$_2$S), 2.67 (3H, s, CONHCH$_3$), 2.61 (2H, m, CHCHCH$_2$S), 2.24 (2H, m, CH$_2$CH$_2$CO$_2$$^t$Bu), 2.04–1.73 (2H, bm, CHCH$_2$CO$_2$$^t$Bu), 1.59 (1H, m, (CH$_3$)$_2$CHCH$_2$), 1.41 (9H, s, CO$_2$C(CH$_3$)$_3$), 1.36 (1H, m, (CH$_3$)$_2$CHHCH$_2$), 1.05 (1H, m, (CH$_3$)$_2$CHC H$_2$) 0.83 (3H, d, J=6.5 (CH$_3$)$_2$CH), and 0.78 (3H, d, J=6.6 Hz, (CH$_3$)$_2$CH).

f) 2S-(4-Hydroxyphenylsulfanylmethyl)-3R-(3-tert butoxycarbonyl-1S-methylcarbamoyl-propylcarbamoyl)- 5-methyl-hexanohydroxamic acid.

2S-(4-Hydroxyphenylsulfanylmethyl)-3R-(2- tert butoxycarbonyl-1S-methylcarbamoyl-propylcarbamoyl)- 5-methyl-hexanoic acid (1.17 g, 2.3 mmol) was taken up in DMF (10 ml) and the solution cooled to 0° C., HOBT (0.34 g, 2.5 mmol) and WSCDI (0.48 g, 2.5 mmol) were added. The reaction mixture was stirred for 2 hours at room temperature. The mixture was once again cooled to 0° C. and hydroxylamine hydrochloride (0.24 g, 3.4 mmol) and NMM (0.35, 3.4 mmol) were added. The mixture was stirred at room temperature overnight. DMF was evaporated under high vacuum and the residue slurried in ether/H$_2$O (1:1, 100 ml). The resulting white precipitate was filtered and dried in vacuo. Further product was isolated by separating the ether layer, evaporating and purifying by column chromatography (acid washed silica gel, 5% methanol/DCM) to yield the title compound (1.02 g, 1.9 mmol, 46%); m.p. 168.9°–168.3° C.; $^1$H NMR $\delta_H$; (methanol-d$_4$), 7.18 (2H, d, J=8.7 Hz, Ar—H), 6.68 (2H, d, J=8.7 Hz, Ar—H), 4.28 (1H, dd, J=5.7, 8.6 Hz, CHCH$_2$CH$_2$), 2.94 (1H, m, CHCHCH$_2$S), 2.78 (1H, dd, J=3.7, 12.9 Hz, CHCHCH$_2$S), 2.68 (3H, s, CONHCH$_3$), 2.56 (1H, dt, J=3.4, 10.9 Hz, CHCHCH2S), 2.35 (1H, dr, J=3.7, 10.9 Hz, CHCHCH$_2$S), 2.25 (2H, m, CH$_2$C H$_2$CO$_2$$^t$Bu), 2.06–1.75 (2H, bm, CH$_2$CH$_2$CO$_2$$^t$Bu), 1.53 (1H, m, (CH$_3$)$_2$CHCH$_2$), 1.41 (1H, m, (CH$_3$)$_2$CHCH$_2$), 1.40 (9H, s, CO$_2$C(CH$_3$)$_3$), 1.02 (1H, m, (CH$_3$)$_2$CHCH$_2$), 0.84 (3H, d, J=6.4 Hz, (CH$_3$)$_2$CH), and 0.79 (3H, d, J=6.5 Hz, (C H$_3$)$_2$CH); $^{13}$C NMR $\delta_C$; (methanol-d$_4$), 175.9, 173.8, 173.7, 171.4, 158.2, 134.3, 125.8, 117.1, 81.9, 53.9, 49.7, 48.1, 41.5, 37.6, 32.7, 28.4, 28.3, 26.9, 26.3, 24.3 and 21.7.

EXAMPLE 13

2S-(4-Hydroxy-phenylsulphinylmethyl)-3R-(3-methoxycarbonyl-1S-methylcarbamoyl-propylcarbamoyl)- 5-methyl-hexanohydroxamic acid.

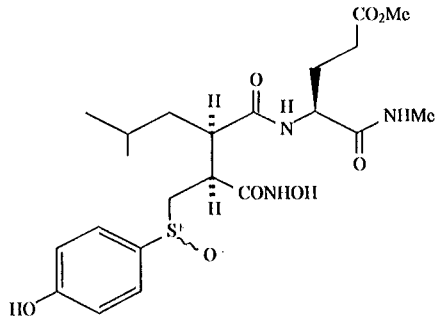

2S-(4-Hydroxy-phenylsulphanylmethyl)-3R-(3-methoxycarbonyl-1S-methylcarbamoyl-propylcarbamoyl)- 5-methyl-hexanohydroxamic acid (0.1 g, 0.207 mmol) was dissolved in methanol (5 ml) and m-chloroperbenzoic acid (0.066 g, 0.227 mmol) added. The resulting solution was allowed to stir at room temperature overnight. Solvent was removed under high vacuum and the residue triturated, with DCM (10 ml). The resulting white precipitate was filtered and washed thoroughly with DCM to provide the title compound (0.07 g, 0.14 mmol, 68%); $^1$H NMR $\delta_H$; (methanol-d$_4$, mixture of diastereomers), 7.52 and 7.46 (2H, d, J=8.7 Hz, Ar—H), 6.91 (2H, d, J=8.8 Hz, Ar—H), 4.27 (1H, m, COCHNH), 3.64 and 3.62 (3H, s, CO$_2$CH$_3$), 3.32 (0.5H, m, CHCH$_2$SO), 3.27 (1H, m, CHCH$_2$SO), 3.05 (0.5H, m, CHCH$_2$SO), 2.75 (1H, m, CH$_2$CHCONHOH), 2.67 (3H, s, CONHCH$_3$), 2.63 (1H, m, CHCHCH$_2$S), 2.29 (2H, m, C H$_2$CH$_2$CO$_2$Me), 1.93 (2H, m, CH$_2$ CH$_2$CO$_2$Me) 1.46 (1H, m, (CH$_3$)$_2$CHCH$_2$), 1.37 (1H, m, (CH$_3$)$_2$CHCH$_2$), 1.01 (1H, m, (CH₃)₂CHCH₂), 1.01 (1H, m, (CH₃)₂CHCH₂), and 0.82 (6H, m, (CH₃)₂CH); ¹³C NMR δ_c; (methanol-d₄), 175.2, 175.1,174.9, 174.7, 174.6,173.7, 173.6,170.3, 162.8, 133.7, 132.7, 131.5, 128.3, 127.4, 117.7, 117.1, 60.0, 58.5, 54.0, 52.3, 47.7, 43.1,43.0, 41.1,41.0, 31.2, 28.2, 26.9, 26.8, 26.3, 24.2, and 21.7.

EXAMPLE 14

2S-(4-Hydroxy-phenylsulphonylmethyl)-3R-(3-methoxycarbonyl-1S-methylcarbamoyl-propylcarbamoyl)-5-methyl-hexanohydroxamic acid

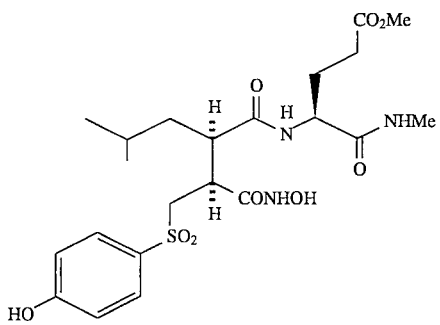

2S-(4-Hydroxy-phenylsulphanylmethyl)-3R-(3-methoxycarbonyl-1 S-methylcarbamoyl-propylcarbamoyl)-S-methyl-hexanohydroxamic acid (0.1 g, 0.207 mmol) was dissolved in methanol (5 ml) and m-chloroperbenzoic acid (0.0.151 g, 0.51 7 mmol) added. The resulting solution was allowed to stir at room temperature overnight. Solvent was removed under high vacuum and the residue triturated, with DCM (10 ml). The resulting white precipitate was filtered and washed thoroughly with DCM to provide the title compound (0.05 g, 0.97 mmol, 48%); ¹H NMR δ_H; (methanol-d₄), 7.67 (2H, d, J=8.7 Hz, Ar—H), 6.91 (2H, d, J=8.8 Hz, Ar—H), 4.22 (1H, m, COCHNH), 3.65 (3H, s, CO₂CH₃), 3.59 (1H, dd, J=14.4, 10.7 Hz, CHCH₂SO₂), 3.00 (1H, d, J=12.7 Hz, CHCH₂SO₂), 2.66 (3H, s, CONHCH₃), 2.63 (1H, m, CHCH₂SO₂), 2.51 (1H, m, CHCHCH₂SO₂), 2.30 (2H, t, J=7.3 Hz, CH₂CH₂CO₂Me), 1.97 (1H, m, CH₂CH₂CO₂Me), 1.87 (1H, m, CH₂CH₂CO₂Me), 1.53 (1H, m, (CH₃)₂CHCH₂), 1.33 (1H, m, (CH₃)₂CHCH₂), 1.01 (1H, m, (CH₃)₂CHCH₂), and 0.80 (6H, t, J=5.9 Hz, (CH₃)₂CH); ¹³C NMR δ_c; (methanol-d₄), 174.9, 174.7, 173.8, 170.0, 164.2, 131.5, 130.5, 117.1,57.0, 53.9, 52.3, 47.7, 42.4, 40.8, 31.2, 28.1,26.8, 26.3, 24.1, and 21.8.

Comparative Example 2S-(4-Hydroxy-phenylsulphanylmethyl)-3R-(3-carboxy-1S-methylcarbamoyl-propylcarbamoyl)-5-methyl-hexanohydroxamic acid.

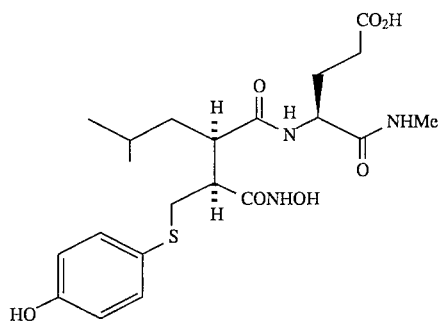

2S-(4-Hydroxyphenylsulfanylmethyl)-3R-(3-tert butoxycarbonyl-1 S-methylcarbamoyl-propylcarbamoyl)-5-methyl-hexanohydroxamic acid (0.2 g, 0.38 mmol) was dissolved in a mixture of DCM and trifluoroacetic acid (1:1, 10 ml) and the resulting solution stirred at room temperature for 1.5 hours. Solvents were evaporated, azeotroping with toluene then chloroform, and the residue triturated with diethyl ether. The resulting white precipitate was filtered and purified by column chromatography (acid washed silica gel, 10% methanol/DCM) to provide the product as a white solid (0.05 g, 0,106 mmol, 28%); ¹H NMR δ_H; (methanol-d₄), 7.20 (2H, d, J=8.7 Hz, Ar—H), 6.68 (2H, d, J=8.7 Hz, Ar—H), 4.28 (1H, m, COCHNH), 2.91 (1H, dd, J=13.0, 11.2 Hz, CHCHCH₂S),2.79 (1H, dd, J=3.7, 13.0 Hz , CHCHCH₂S), 2.67 (3H, s, CONHCH₃), 2.55 (1H, dt, J=3.3, 10.6 Hz, CHCHCH₂S), 2.32 (3H, m, CHCHCH₂S and CH₂CH₂CO₂H), 1.93 (2H, bm, CH₂CH₂CO₂H) 1.48 (1H, m, (CH₃)₂CHCH₂), 1.39 (1H, m, (CH₃)₂CHCH₂), 1.01 (1H, m, (CH₃)₂CHCH₂), 0.84 (3H, d, J=6.4 Hz, (CH₃)₂CH), and 0.79 (3H, d, J=6.5 Hz, (CH₃)₂CH); ¹³C NMR δ_C; (methanol-d₄), 176.2, 175.9, 173.8, 171.3, 158.2, 134.5, 125.7, 117.1, 54.0, 48.1, 41.5, 37.4, 31.3, 28.2, 26.8, 26.2, 24.3, and 21.7.

Biological Example A

The ability of example compounds of the invention to inhibit the release of TNF was investigated. The assay is based on the ability of phorbol myristate acetate (PMA) to stimulate the release of TNF α from a human monocytic cell line, U937.

U937 cells cultured in RPMI 1640 medium +5% foetal calf serum are centifuged at 1000×g for 5 minutes and then resuspended in medium at 2×10⁶/mi. 1 ml of cell suspension is aliquoted into individual wells of 24-well plates. Test compounds are dissolved in dimethyl sulphoxide (DMSO) at a stock concentration of 100 mM, then diluted to 50×the final required concentration with RPMI 1640 medium. 20 μl of the diluted compounds are added to U937 cells in duplicate wells. TNF α release is stimulated by addition of PMA to the cells at a final concentration of 50 nM. Appropriate control cultures are set up in duplicate. The plates are incubated for 18 hours at 37° C., 5% CO₂, then centrifuged at 1000×g for 5 minutes. A specific ELISA for TNF α obtained from British Bio-technology Products Limited, Abingdon, England is used to measure TNF α levels in the culture supernatants The average concentration of test compound which inhibits the release of TNF α by 50% relative to the control culture was assessed. The compounds of examples 2, 3 and 12 above were tested and had IC₅₀ values less than 50 μM.

Biological Example B

The compound of Example 3 was assessed for its ability to inhibit release of endotoxin induced TNF production in vivo.

Male New Zealand rabbits, 2.5–3.0 kg, were anaesthetised with sodium pentobarbitone, 30 mg.kg$^{-1}$ via a marginal ear vein which was maintained by infusion at 18 mg.kg$^{-1}$.hr$^{-1}$ via a jugular vein. Following tracheotomy, the animals were ventilated, to maintain arterial blood $PO_2$ between 35 and 40 mmHg, and oxygen was added to the inspired air to maintain arterial blood $PO_2$ above 100 mmHg. Both femoral veins were cannulated for the administration of endotoxin (LPS) and the infusion of test compound, 2.5 mg.kg$^{-1}$.hr$^{-1}$ at a rate of 6 ml.hr$^{-1}$, 15 minutes before the administration of LPS, 40 µg.kg$^{-1}$ i.v. bolus. Blood samples were collected from a femoral artery just before and at 30 minute intervals after the administration of LPS for a period of 4 hours.

The biological activity of TNF in serum test samples was determined using a cytotoxicity assay as described in Mathews, N. and Neale, M. L. in Lymphokines and Interferons, a Practical Approach, Eds. M. J. Clements, A. G. Morris, and A. J. H. Gearing, IRL Press, Oxford, UK.

100 µl volumes of L929 cell suspension at $10^5$ cells/ml were dispensed into 96-well microtitre plates. The plates were incubated overnight to allow formation of an even monolayer. A series of dilutions of the test rabbit serum was made in a culture medium containing 2 µg/ml of actinomycin D to give a final concentration of 1 µg/ml when added to the cells. The L929 cells were incubated for 24 hours in the presence of test samples, and serially diluted human TNF α was used as the assay standard. After the incubation period, dead cells were removed by washing briefly with phosphate buffered saline, and remaining cells were fixed with 4% formaldehyde for 10 minutes. After washing the plates with water to remove the fixative, the cells were stained by the addition of 50 µl of 1% crystal violet to each well for 5 minutes. The plates were washed extensively with water and dried. Cells were solubilised by the addition of 100 µl/well of 30% acetic acid and the OD at 550 nm was determined. The TNF level in units/ml in the test samples was determined from the human TNF α standard curve, where 1 unit is the equivalent of 1 pg/ml human TNF α.

| Results: Time (hrs) from | Average % change in serum TNF level | |
|---|---|---|
| from LPS bolus IV injection | LPS (n = 5) | LPS + test compound (n = 4) |
| 0 | 0 | 0 |
| 1 | +65 | -58 |
| 2 | +55 | -65 |
| 3 | -30 | -99 |
| 4 | -100 | -100 |

Biological Example C

The potency of compounds of Examples 1,2, 3 and 12 to act as inhibitors of collagenase was determined by the procedure of Cawston and Barrett, (Anal. Biochem., 99, 340–345, 1979), hereby incorporated by reference, whereby a 1 mM solution of the compound being tested, or a dilution thereof, was incubated at 37° for 16 hours with collagen and collagenase (buffered with 25 mM Hepes, pH 7.5 containing 5mM $CaCl_2$, 0.05% Brij 35 and 0.02% $NaN_3$). The collagen was acetylated $^{14}C$ collagen prepared by the method of Cawston and Murphy, (Methods in Enzymology, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity ($IC_{50}$).

The potency of compounds of Examples 1,3 and 12 to act as inhibitors of stromelysin was determined by the procedure of Cawston et al, (Biochem. J., 195, 159–165, 1981), hereby incorporated by reference, whereby a 1 mM solution of the compound being tested, or a dilution thereof, was incubated at 37° for 16 hours with stromelysin and $^{14}C$ acetylate casein (buffered with 25 mM Hepes, pH 7.5 containing 5 mM $CaCl_2$, 0.05% Brij 35 and 0.02% $NaN_3$). The casein was acetylated $^{14}C$ casein prepared by the method of Cawston et al (ibid). The stromelysin activity in the presence of 1 mM of the test compound, or a dilution thereof, was compared to activity in a control devoid of inhibitor and the result reported below as that of inhibitor concentration effecting 50% inhibition of the stromelysin activity ($IC_{50}$).

| | Results: | |
|---|---|---|
| Compound | Collagenase IC50 | Stromelysin IC50 |
| Example 1 | 20 nM | 250 nM |
| Example 2 | 15 nM | . . |
| Example 3 | 9 nM | 50 nM |
| Example 12 | 20 nM | 40 nM |

We claim:
1. A compound of formula (I):

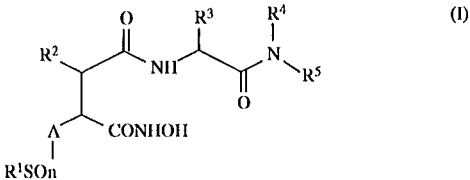

wherein:

$R^1$ represents hydrogen or an $(C_1-C_6)$alkyl, $(C_1-C_6)$alkoxycarbonyl$(C_1-C_6)$alkyl, phenyl, substituted phenyl, phenyl$(C_1-C_6)$alkyl, heterocyclyl, $(C_1-C_6)$alkylcarbonyl, phenacyl or substituted phenacyl group;

$R^2$ represents hydrogen or a $(C_1-C_6)$alkyl, $(C_2-C_6)$alkenyl, phenyl$(C_1-C_6)$alkyl, cycloalkyl$(C_1-C_6)$alkyl or cycloalkenyl$(C_1-C_6)$alkyl group, $R^3$ represents a group —$CH_2CO_2(C_1-C_4)$alkyl or —$CH_2CH_2CO_2(C_1-C_4)$alkyl;

$R^4$ represents hydrogen or a $(C_1-C_6)$alkyl or phenyl$(C_1-C_6)$alkyl group;

$R^5$ represents hydrogen or a methyl group;

n is 0, 1 or 2;

and A represents a $(C_1-C_6)$hydrocarbon chain optionally substituted with one or more $(C_1-C_6)$alkyl, phenyl, or substituted phenyl groups;

or a salt, solvate or hydrate thereof.

2. A compound as claimed in claim 1 wherein the chiral center adjacent to the substituent $R^3$ has S stereochemistry.

3. A compound as claimed in claim 1 wherein the chiral center adjacent to the substituent $R^2$ has R stereochemistry.

4. A compound as claimed in claim 1 wherein the chiral center adjacent to the —CONHOH moiety has S stereochemistry.

5. A compound as claimed in claim 1 wherein $R^1$ represents hydrogen or an $(C_1–C_6)$alkyl, phenyl, thienyl, substituted phenyl, benzyl, acetyl or phenacyl group.

6. A compound as claimed in claim 5 wherein $R^1$ is 4-methoxyphenyl, 4-hydroxyphenyl, 4-aminophenyl, thien-2-yl, or t-butyl.

7. A compound as claimed in claim 1 wherein $R^2$ represents a $(C_3–C_6)$alkyl group.

8. A compound as claimed in claim 1 wherein $R^4$ represents a $(C_1–C_4)$alkyl group.

9. A compound as claimed in claim 1 wherein $R^5$ represents a hydrogen atom.

10. A compound as claimed in claim 1 wherein A represents a methylene group —$CH_2$—.

11. A compound as claimed in claim 1 wherein n=0.

12. A compound as claimed in claim 1, selected from the group consisting of:

3R-(3-Methoxycarbonyl-1S-methylcarbamoyl-propylcarbamoyl)-5-methyl-2S-phenylsulfanylmethyl hexanohydroxamic acid;

3R-(3-Methoxycarbonyl-1S-methylcarbamoyl-propylcarbamoyl)-5-methyl-2S-(thien- 2-ylsulfanylmethyl)-hexanohydroxamic acid;

2S-(4-Methoxy-phenylsulfanylmethyl)-3R-(3-methoxycarbonyl-1S-methylcarbamoyl-propylcarbamoyl)- 5-methyl-hexanohydroxamic acid;

2S-(4-Amino-phenylsulfanylmethyl)-3R-(3-methoxycarbonyl-1S-methylcarbamoyl-propylcarbamoyl)- 5-methyl-hexanohydroxamic acid;

2S-(Ethylsulfanylmethyl)-3R-(3-methoxycarbonyl-1S-methylcarbamoyl-propylcarbamoyl)- 5-methyl-hexanohydroxamic acid;

2S-(Acetylsulfanylmethyl)-3R-(3-methoxycarbonyl-1S-methylcarbamoyl-propylcarbamoyl)- 5-methyl-hexanohydroxamic acid;

2S-(Benzylsulfanylmethyl)-3R-(3-methoxycarbonyl-1S-methylcarbamoyl-propylcarbamoyl)- 5-methyl-hexanohydroxamic acid;

2S-(tert-Butylsulfanylmethyl)-3R-(3-methoxycarbonyl-1S-methylcarbamoyl-propylcarbamoyl)- 5-methyl-hexanohydroxamic acid;

2S-Thiomethyl-3R-(3-methoxycarbonyl-1S-methylcarbamoyl-propylcarbamoyl)- 5-methyl-hexanohydroxamic acid;

2S-(4-Hydroxyphenylsulfanylmethyl)-3R-(2-tert-butoxycarbonyl-1S-methylcarbamoyl-ethylcarbamoyl)- 5-methyl-hexanohydroxamic acid;

2S-(4-Hydroxy-phenylsulphinylmethyl)-3R-(3-methoxycarbonyl-1S-methylcarbamoyl-propylcarbamoyl)- 5-methyl-hexanohydroxamic acid;

2S-(4-Hydroxy-phenylsulphonylmethyl)-3R-(3-methoxycarbonyl-1S-methylcarbamoyl-propylcarbamoyl)- 5-methyl-hexanohydroxamic acid;
and salts hydrates and solvates thereof.

13. 2S-(4-Hydroxyphenylsulfanylmethyl)-3R-(3-methoxycarbonyl-1S-methylcarbamoyl-propylcarbamoyl)-5-methyl-hexanohydroxamic acid and salts hydrates and solvates thereof.

14. 2S-(4-Hydroxyphenylsulfanylmethyl)-3R-(3-tert butoxycarbonyl- 1S-methylcarbamoyl-propylcarbamoyl)-5-methyl-hexanohydroxamic acid and salts hydrates and solvates thereof.

15. A method for treatment or prophylaxis of diseases or conditions mediated by TNF or MMPs in mammals, which method comprises administering to the mammal an effective amount of a compound as claimed in claim 1.

16. A method as claimed in claim 15, wherein the disease or condition is inflammation, fever, cardiovascular effects, haemorrhage, coagulation and acute phase response, cachexia and anorexia, acute infections, shock states, graft versus host reactions or autoimmune disease.

17. A method as claimed in claim 15, wherein the disease or condition is rheumatoid arthritis, osteoarthritis, periodontitis, gingivitis, corneal ulceration, tumour growth, tumour angiogenisis or tumour invasion by secondary metastases.

18. A method as claimed in claim 15, wherein the mammal is a human.

19. A pharmaceutical or veterinary composition comprising a compound as claimed in claim 1 together with a pharmaceutically or veterinarily acceptable excipient or carrier.

20. A process for preparing a compound of general formula (I) as defined in claim 1, comprising:

(a) coupling an acid of general formula (II)

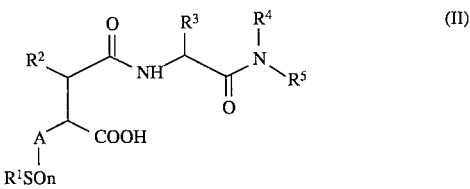

or an activated derivative thereof with hydroxylamine, O-protected hydroxylamine, or a salt thereof, $R^1$, $R^2$, $R^3$, $R^4$, $R^5$, A and n being as defined in claim 1, except that any substituents in $R^1$, $R^2$, $R^3$, and A which are potentially reactive with hydroxylamine, O-protected hydroxylamine or their salts may themselves be protected from such reaction, then removing any protecting groups from the resultant hydroxamic acid moiety and from any protected substituents in $R^1$, $R^2$, $R^3$ and A or (b) esterifying a compound of formula (IIA)

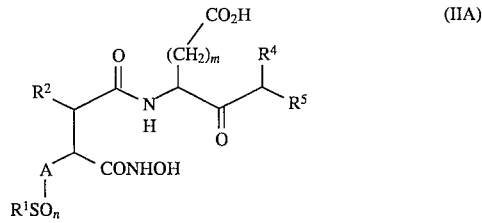

wherein m=1 or, and $R^1$, $R^2$, $R^4$, $R^5$, A and n are as defined in claim 1, with an alcohol of formula HO$(C_1–C_4)$alkyl; and (c) optionally after step (a) or (b) converting a compound of general formula (I) into another compound of general formula (I).

21. A process as claimed in claim 20 wherein an activated derivative of the acid (II) is used, and that activated derivative is the pentafluorophenyl, hydroxysuccinyl, or hydroxybenztriazyl ester.

22. An acid of general formula (II)

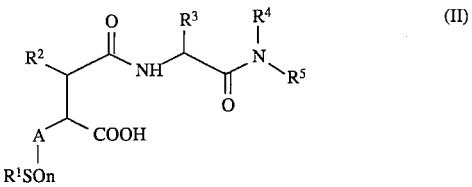

wherein $R^1$, $R^2$, $R^3$, $R^4$, $R^5$, A and n, are defined in claim 1, and the stereochemistry of the chiral center adjacent the $R^2$ group is R, the stereochemistry of the chiral center adjacent the $R^3$ group is S, and the stereochemistry of the chiral center adjacent the —COOH group is S.

23. An acid of general formula (IIA)
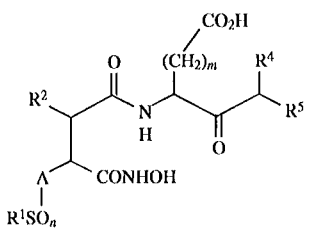
wherein m=1 or 2, and $R^1$, $R^2$, $R^4$, $R^5$, A and n are as defined in claim 1, and the stereochemistry of the chiral center adjacent the $R^2$ group is R, the stereochemistry of the chiral center adjacent the $R^3$ group is S, and the stereochemistry of the chiral center adjacent the —CONHOH group is S.
* * * * *